(12) United States Patent
Kirby et al.

(10) Patent No.: US 6,444,234 B1
(45) Date of Patent: Sep. 3, 2002

(54) COMPOSITIONS FOR RAPID AND NON-IRRITATING TRANSDERMAL DELIVERY OF PHARMACEUTICALLY ACTIVE AGENTS AND METHODS FOR FORMULATING SUCH COMPOSITIONS AND DELIVERY THEREOF

(76) Inventors: Kenneth B Kirby, 8631 Uranus Ter., Lake Park, FL (US) 33403; Berno I. R. Pettersson, Jr., 1100 3rd St. Meadowdale Sub-Division, Perry, GA (US) 31069

( * ) Notice: Subject to any disclaimer, the term of this patent is extended or adjusted under 35 U.S.C. 154(b) by 0 days.

(21) Appl. No.: 09/381,095

(22) Filed: May 11, 2000

Related U.S. Application Data
(60) Provisional application No. 60/091,910, filed on Jul. 7, 1998.

(51) Int. Cl.$^7$ .............................................. A01N 35/78
(52) U.S. Cl. ...................... 424/725; 424/449; 514/946; 514/947
(58) Field of Search ............................... 424/195.1, 449, 424/2.14, 725; 514/946, 947, 783, 937

(56) References Cited

U.S. PATENT DOCUMENTS

| | | |
|---|---|---|
| 4,002,775 A | 1/1977 | Kabara |
| 4,330,551 A | 5/1982 | Stout et al. |
| 4,746,515 A | 5/1988 | Cheng et al. |
| 4,764,379 A | 8/1988 | Sanders et al. |
| 4,777,047 A | 10/1988 | Bauer et al. |
| 4,788,062 A | 11/1988 | Gale et al. |
| 4,789,547 A | 12/1988 | Song et al. |
| 4,820,720 A | 4/1989 | Sanders et al. |
| 4,844,901 A | 7/1989 | Keplinger et al. |
| 4,855,294 A | 8/1989 | Patel et al. |
| 5,053,222 A | 10/1991 | Takasu et al. |
| 5,077,284 A | 12/1991 | Loria et al. |
| 5,096,715 A | 3/1992 | Sinclair |
| 5,164,416 A | 11/1992 | Nagai et al. |
| 5,230,897 A | 7/1993 | Griffin et al. |
| 5,240,932 A | 8/1993 | Morimoto et al. |
| 5,324,521 A | 6/1994 | Gertner et al. |
| 5,332,577 A | 7/1994 | Gertner et al. |
| 5,362,479 A | 11/1994 | Yamada et al. |
| 5,460,821 A | 10/1995 | Masiz |
| 5,523,090 A | 6/1996 | Znaiden et al. |
| 5,529,769 A | 6/1996 | Cho et al. |
| 5,562,910 A | 10/1996 | Daynes et al. |
| 5,653,970 A | 8/1997 | Vermeer |
| 6,019,997 A * | 2/2000 | Scholz et al. |

OTHER PUBLICATIONS

Dasarthy, et al., J. Cellular Physiology, 1991, 148(2):327–335, Abstract (Database EBMASE in STN, AN 91290543).

T.K. Ghosh, et al., Methods of Enhancement of Transdermal Drug Delivery, Parts I, IIa, & IIb, Chemical Permeation Enhancers, Pharm. Tech. 17 (3):72–98M, 17 (4) :62–89m and 17(5):68–76 (1993).

Crouch, James E., Functional Human Anatomy, Lea & Fibiger, LOCCN 65–12968, Chapter 6, pp. 88–97, 1965..

K. Tojo, Random Brick Model for Drug Transport Across Stratum Corneum, J. Pharm. Sci., 76:889–891.

S.D. Roy, Preformulation Aspects of Transdermal Delivery Systems, Interpharm Press, Inc., Buffalo Grove, IL, 1997.

K. Gjesdal, et al., Transdermal Nitrate Therapy . . . , Brit. J. Clin. Pharmacol. 31:560–562 (1991).

K. Tojo, The Prediction of Transdermal Permeation . . . , Interpharm Press, Buffalo Grove, IL, 1997.

I. Diez, et al., A Comparative In Vitro Study of Transdermal Absorption . . . , J. Pharm. Sci. 80:931–934 (1991).

W.R. Pfister, et al., Permeation Enhancer Compatible with Transdermal . . . , Pharm. Tech. 14(9):132–140, 14(10):56–60.

C.D. Vaughn, Using Solubility Parameters in Cosmetic Formulations, J. Soc. Cosmet. Chem. 36:319–333 (1985).

J.W. Streilein, In: Immune Mechanisms in Cutaneous Diseases, Ed. D.A. Norris, Marcel Dekker, Inc., New York, pp. 73–96 (1989).

J. Ademola, et al., Safety Assessment of Transdermal and Topical Dermatological Products In: Transdermal and Topical Drug Delivery Systems, Interpharm Press, Inc., Buffalo Grove, IL (1997).

P. Liu, et al., Quantitative Evaluation of Ethanol Effects on Diffusion . . . , Pharm. Res. 8:865–872 (1991).

(List continued on next page.)

Primary Examiner—Christopher R. Tate
Assistant Examiner—Michele C. Flood
(74) Attorney, Agent, or Firm—McHale & Slavin

(57) ABSTRACT

Pharmaceutical compositions for the transdermal administration of a medicament or other active agent by topical application of the composition to the skin of humans or other animals are described. Methodology for formulating such compositions which provide for very rapid uptake of the medicament and transmigration into and through the skin to either fatty tissues or the vascular system, while minimizing irritation to the skin and/or immunological response, is based on a transdermal delivery system (TDS) wherein the medicament is modified to form a true solution in a complex formed from particular solvents and solvent and solute modifiers in combination with skin stabilizers. Uptake of the medicament is further facilitated and made more rapid by including Forskolin or other source of cellular energy, namely induction of cAMP or cGMP. Selection of specific solvents and solvent and solute modifiers and other functional ingredients and the amounts thereof are chosen such that there is a balance between the sum of the mole-moments [(molar amount of each individual ingredient)×(dipole moment of that ingredient)] of the delivery system and the sum of the moler moments of the composition in which the medicament is dissolved. Preferably, the van der Waals forces of the delivery system is also similarly matched to the van der Waals forces of the total composition, namely, delivery system plus active agent.

4 Claims, 4 Drawing Sheets

OTHER PUBLICATIONS

Lubert Stryer, Biochemistry, 2nd Edition, Chapter 35, pp. 839–858, W.H. Freeman, Co., New York, (1981).

Kenneth B. Seamon, et al., Forskolin: Unique Diterpene Activator of Adenylate Cyclase . . . , PNAS, vol. 78, No. 6, pp. 3363–3367 (Jun. 1981).

Hermann P.T. Ammon, et al., Forskolin: From Ayurvedic Remedy to a Moder Agent; Planta Medica, pp. 473–476 (1985).

World Class Help From Rain Forest Herb . . . Cat's Claw, ACCM, vol. II, No. 2, Mar. 1996.

Buyuktimikin, et al., Chapter 11, in Transdermal and Topical Drug Delivery System, Ed. T. K. Gosh, et al., Interpharm Press, Inc., pp. 357, 433–434.

W. Kreutner, et al., Eur. J. of Pharmacology, 1985, 111:1–8.

G. Marone, et al., Agents and Actions, 1986, 18:96–99.

N.J. de Souza, et al., Medicinal Research Reviews, 1983, 3:201–219.

K.C. Agarawal, et al., Int. J. Cancer, 1983, 32:801–804.

J. Caprioli, et al., The Lancet, Apr. 30, 1983, pp. 958–960.

E. Lindner, et al., Hoechst Aktiengesellschaft, Frankfurt/Main(Germany) Positive Inotropic and Blood Pressure Lowering Activity . . .

M.P. Dubey, et al., J. of Ethnopharmacology, 1981, 3:1–13.

H.W. Hadley, et al., Alt. Med. Rev., 1998, 3:361–366.

R.O. Potts, et al., J. Drug Target, 1995, 3:247–251 (Abstract).

P. Xu, et al., Crit. Rev. Ther. Drug Carrier Syst., 1991, 8:211–236 (Abstract).

* cited by examiner

COMPOSITIONS FOR RAPID AND NON-IRRITATING TRANSDERMAL DELIVERY OF PHARMACEUTICALLY ACTIVE AGENTS AND METHODS FOR FORMULATING SUCH COMPOSITIONS AND DELIVERY THEREOF

CROSS-REFERENCE TO RELATED APPLICATIONS

This is the §371 National Phase entry of International PCT Application PCT/US99/15297, filed Jul. 7, 1999, which in turn claims priority from U.S. application Ser. No. 60/091,910 filed Jul. 7, 1998.

FIELD OF THE INVENTION

This invention relates to transdermal delivery of active agents, including pharmaceuticals, cosmetics, nutrients, and the like, across the skin barrier of humans or other animals and to a method for developing new transdermal delivery systems for any particular polar or non-polar active agent of small or large molecular size, which delivery systems are capable of rapidly delivering the active agent to a targeted location systemically or locally.

BACKGROUND OF THE INVENTION

The pharmaceutical industry is actively seeking to develop new and improved modes of drug delivery to enhance the effectiveness of particular drugs, including, targeting the drug to the intended site, reducing dosage, decreasing toxicity, and the like. Major efforts are underway in molecule stabilization for parenteral applications, extended release modalities for enteral drugs and photoactivated chemotherapeutic molecules, for example. Delivery of medications via transdermal drug delivery (TDD) systems (patches) has also seen dramatic developments. For example, it is now generally agreed that chemical modification of the barrier properties of the skin is a safe and effective method to enhance penetration of medicaments (Ref. 1). However, to some extent it seems that this mode of delivery has reached its technological limits.

The present inventors have analyzed the TDD systems and have been able to identify certain limiting factors. These include, for example, limitations to compounds which are lipophilic medicaments;

medicaments with an effective therapeutic dose of $\leq 1$ mg per day;

medicaments having a melting point below about 150° C.;

medicaments having a molecular weight of from less than about 300 to about 500 Daltons (the larger the molecule, the less is the amount deliverable via the stratum corneum);

molecules which do not elicit a rapidly cascading immune response when transmigrating the skin.

With regard to the molecular weight limitation, currently commercially available TDD systems deliver molecules with molecular weights less than about 340 D and in amounts generally less than about 1.0 mg per 24 hours.

Additionally, candidate medicaments should also, preferably, be soluble in ethanol and/or isopropanol and/or glycols or dimethyl sulfoxide (DMSO) and should not be chemically altered by solubilization. Another potentially limiting factor is for compounds which can have efficacy at relatively small doses introduced systemically via the capillary net of the dermis. Main limiting factors thus include molecule size and irritation potential of the medicament plus solvent(s) and other components.

The inventors have also analyzed the chemistry and chemical structures of active ingredients and carriers of transdermal delivery systems and have found other limiting factors leading to the limited success of transdermal drug delivery. Most typically it has been observed that these systems have not been widely acceptable because the drug carriers chemically bond with the medicament resulting in non-bioavailable compounds transmigrating the skin; or/and the carrier, e.g., DMSO, reduces the medicament yielding a non-bioavailable or non-bio-equivalent compound or creates toxic by-products of transmigration.

Only about 1% or less of known medicaments would not be excluded for administration by a TDD system based on the above limiting factors. Still further, TDD systems currently available are usually subject to broadly varying results as a function of the circulation efficiency of the patient. Age, size and weight of the patient all impact how efficiently these systems perform. For most TDD systems there is virtually no drug penetration for the first hour after application and often 24 to 48 hours are required to achieve a therapeutic level.

The anatomy and physiology of the integument was analyzed to understand the complex protective mechanism of physical, biochemical and bio-electrical gradients which work to minimize the penetration of foreign substances and sensitize the organism to react more rapidly and aggressively to future exposures. As a result of this analysis it is postulated that:

The primary pathway of transdermally delivered drugs is paracellular, i.e., around the cells, then through the elastin glue.

The glue-like compound, elastin, composed of collagen and hyaluronic acid and other lipids, which occupies the interstices between the cells of the top-most layer of the skin (i.e., the epidermis, including, e.g., stratum corneum (SC), lucidum, granulosum, spinosum) must be dissolved (or otherwise disrupted) in order for a medicament or other active agent, dissolved in a solvent, to transmigrate through viable skin (VS) to the subcutaneous tissues where the cutaneous plexi of the capillary net can be reached and/or deeper penetration achieved (Ref. 2). When the elastin is dissolved, other agents may then transmigrate the outer layers, so the body immediately begins to attempt to repair the damage caused by the dissolution.

Skin penetration enhancers (SPE) which delipidize can reduce the barrier capacity of the SC as a function of species of enhancer and its concentration. Permeability may often be adjusted by modifying the HLB of the enhancer (Ref. 3).

Capillary circulation acts as a sink for the medicament, thus maintaining a steep chemical potential gradient across the skin (Ref. 4).

Diffusivity of a drug molecule is dependent on properties of both the medicament and the medium (carrier) The diffusivity in liquid media, in general, tends to decrease with increased molecular volume (Ref. 5).

The rate of skin penetration is a function of (1) the Diffusion Coefficient, (2) the barrier partitioning tendencies, (3) binding affinities, and (4) the rate of metabolism of the medicament by the skin (Ref. 6). The Diffusion Coefficient of the medicament is influenced by (1) molecular weight, (2) molecular structure, (3) additives, (4) rate of metabolism of the medicament by the skin. Diffusion is also dependent on the carrier, with diffusivity decreasing with increased molecular volume.

An optimum HLB is required for a medicament to penetrate efficiently. The optimum HLB may be predicted by plotting the log (Permeability Coefficient) vs. log (Oil and Water Partition Coefficient) of the medicament for the SC and the VS (Ref. 4).

Highly lipophilic drugs bind readily in the VS and, therefore, dissolution into the blood is minimal (Ref. 6). Therefore, highly lipophilic drugs must be shielded to inhibit such binding.

Skin metabolizes drugs effectively, so metabolism issues in the skin, such as, enzyme saturation and/or inhibition, medicament/metabolite fluxes (e.g., how rapidly and completely does the drug metabolize to a different form) should be taken into account.

Un-ionized species of medicaments transmigrate more readily (Ref. 4). Generally, un-ionized species are two orders of magnitude more permeable than their ionized form.

The Hildebrand Solubility Parameter (HSP) is useful for predicting the mutual solubility and compatibility of medicaments, SPEs, and polymers and for optimizing skin permeability (Ref. 7). The HSP describes the attractive forces between molecules and is defined as the square root of the Cohesive Energy Density (Ref. 8). The HSP spans a range where the low value is associated with lipophilic compounds and a high value with hydrophilic compounds. The solubility parameter can be further partitioned into polar, non-polar, dispersive, and hydrogen bonding components which are useful to predict molecular interactions between compounds (Ref. 9). The solubility parameter or Cohesive Energy Density is synonymous with lipophilic/hydrophilic properties (Ref. 4). Dipole moment is also an expression of the Cohesive Energy Density.

Transient increases in cutaneous blood flows may result in increased systemic absorption of the drug from the depot of the TDD (Ref. 5).

Furthermore, cellular biological issues were reviewed in order to identify and categorize membrane and organelle functions, both in the integument and in other tissues, which might be subject to variations which might help or hinder tissue transmigration of a medicament and solvent. In particular, it is proposed that, SPE's and solvent modification systems can cause irritation apart from the medicament they are delivering. Chronic exposure to irritants has the potential to become carcinogenic and, therefore, care must be taken in the design and testing of TDD systems.

Efferent tactile corpuscles of nerves form an "early warning detection system." The cellular and humoral components of this peripheral immune surveillance system present in the skin are responsible for the genesis of a hapten-specific, cell-mediated immune response following the penetration of the skin by, and complexing of skin components with, sensitizing chemicals and drugs (Ref. 10). If a drug is able to penetrate the skin and covalently bind with amino acids in the skin, dermal hypersensitivity is possible. If the hapten-protein conjugate is of sufficient size to be recognized as a foreign antigen, a specific antibody or cell-mediated immune response will ensue that sensitizes the skin's immune system to the hapten molecule. Upon re-exposure of the skin to the sensitizing chemical, a dermal hypersensitivity reaction of the delayed onset type 4 hypersensitization may be elicited (Ref. 11). Effective transmigration must be able to elude or minimize this response to effectuate repeated challenge without anaphylaxis or ACD sensitization. Avoiding binding in the skin is, therefore, an important objective.

Some SPE's reduce residence time of the medicament in the skin and reduce the extent of cutaneous metabolism thereby reducing exposure to the medicament or metabolite. The faster the medicament moves, the less metabolism takes place. Rate and extent of metabolism in the liver and skin on a unit basis are virtually the same and disposition is the same by IV dosage (Ref. 12).

Virtually any solvent used to dissolve and form a medium for drugs is toxic on the cellular level at the concentrations required, therefore, the tissues are effectively challenged with eliminating the medicament and the solvent, thereby draining substantial energy from the system.

Most challenges force the cell to expend adenosine triphosphate (ATP) to move compounds across gradients or to maintain barrier integrity against transmigration by compounds.

Adenylate cyclase substrate for the cAMP system, when varied, can yield substantial changes in a cell's tolerance for, and ability to recover from, the challenge of dermal transmigration, accelerating the time line to a steady, bioavailable equilibrium of the medicament (Ref. 13).

Topical, transdermal drug delivery modalities, nevertheless, have certain apparent benefits so that there is still much activity not only in the patch systems but also in the non-patch transdermal delivery systems, such as gels, ointments, and other topical formulations.

OBJECTS OF THE INVENTION

Accordingly, it is a primary object of the invention to provide compositions for the rapid transdermal administration of medicaments or other active agents to humans or other animals which does not require use of a "patch" delivery system.

Another object of the invention is to provide compositions effective for transdermal delivery of active compounds not previously amenable to this route of administration, particularly for pharmacological agents having molecular weights in excess of about 300 D and/or at dosages in excess of 0.25 mg/cm$^2$ per day, especially, in excess of about 1 mg/cm$^2$/day.

It is another object of the invention to provide topical compositions for transdermal delivery of active agents for humans and other animals which leaves the barrier properties of the skin substantially intact and which invokes only minimal or substantially no immune response at the site of application.

Still another object of the invention is to provide a standardized solvent/carrier base system which is useful for forming topically applied compositions for transdermal administration of many different medicaments with none or only minimal modification required to achieve a true solution of the medicament and effective, safe, and rapid transmigration of the medicament through intact skin.

Another object of the invention is to provide safe and effective compositions for transdermal administration of a variety of medicaments and other active agents of low or high molecular weight which allows repetitive applications over short or long periods of time at the same site on the intact skin without causing damage to or immunological reaction by the skin.

It is another object of the invention to provide a method for formulating safe and effective compositions for topical transdermal application of an active agent by matching the solvent/carrier system for the particular active agent which will allow the agent to transmigrate across the skin barrier with no or only minimal immunological response at the site of application and without degrading the chemical structure or bioactivity of the active agent.

These and other objects of the invention will become clearer upon review of the following more detailed description and specific embodiments, and with the aid of the accompanying drawings in which:

SUMMARY OF THE INVENTION

Figure 1:
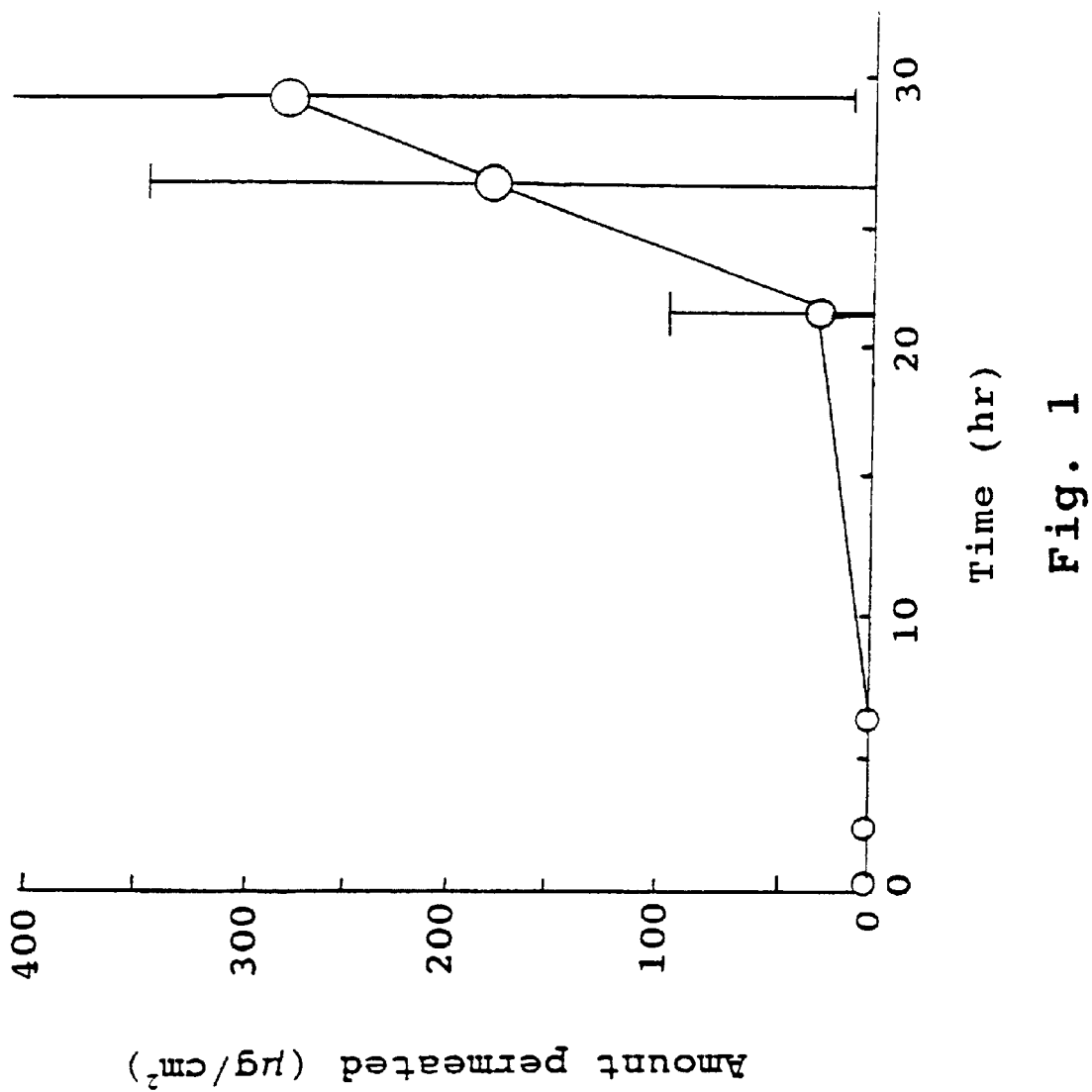
FIG. 1 is a graphical representation of the results obtained in Example 13, for the flux ($\mu g/cm^2$) vs. time (h), of morphine (as morphine sulfate) under open (lotion) conditions using the topical delivery system SDS-L.

Based on the above observations and reviews of the overall biological systems of the skin and vascular organs, including at the cellular and microbiological levels, it was concluded that an effective and "universal" transdermal drug delivery system (as used herein, unless the context indicates otherwise, the reference to "drug" delivery is intended to include not only drugs, medicines, pharmacologicals, and other biologically active ingredients, but also other active agents, such as, cosmetically active substances, nutrient substances and the like) should have the following characteristics and features:

ability to dissolve and emulsify the active agent down to individual molecules (true solutions) in a carrier which remains liquid long enough to penetrate the epidermis;

remains stable as formulated and not form an irreversible complex with other substances;

does not damage the skin with repeated use;

releases the active agent appropriately and does not alter the agent or leave as residual compounds which might be sensitizing.

The present invention provides a topical formulation for the transdermal delivery of an active agent which addresses the design of the integument as a biologically responsive physical, chemical and bioelectrical barrier against the active agent(s) and solvent(s). Accordingly, solvent(s) and modifying component(s) are selected so that permanent or strong covalent bonds with the medicament or other active agent are not formed, while the complexes that are formed facilitate movement of the complex past the viable skin to its optimal targeted internal circulation system of blood, lymph or neural, or beyond these systems, wherein the complexers and modifiers are readily stripped from the active agent at the intended site of application, thereby leaving the active agent free to seek the appropriate receptors once released.

At the same time, the formulations according to this invention are designed to modify the active agent and solvent(s) to minimize their reactivity and sensitizing characteristics as well as making the active agent more "slippery" thereby facilitating transmigration through the skin. By facilitating the transmigration and increasing the rate of diffusion of the active agent and other system components through the skin the less time the formulation will have to remain in the tissues and the lower the physiological response. In part, this is accomplished by selecting solvent (s) and modifier(s) to provide a true solution, namely a solution of the various components in the solvent system on a molecular level, while at the same time forming a protective "coating" or temporary complex with the active agent to facilitate its intact transmigration through the skin.

The present invention also provides transdermal drug delivery systems which may include a substance which can assist the skin in repairing damage which is caused by the transmigration of the delivery system.

In one broad aspect of the invention there is provided a topical formulation for rapid transdermal delivery of an active agent through intact skin wherein the formulation includes (1) active agent, (2) solvent system in which the active agent is soluble, and (3) a substance capable of in vivo stimulation of adenosine 3',5'-cyclic monophosphate (CAMP) or cyclic guanosine 3',5'-monophosphate (CGMP).

The substance capable of in vivo cAMP stimulation is, preferably, an extract of *Coleus Forskholi*, especially a labdane diterpene, such as Forskolin, or colforsin or coleonol.

The formulation may and, preferably will, also include one or more additional ingredients effective for enhancing percutaneous absorption of the active agent in its intact, bioactive form. Such additional agents include, for example, one or more of modifiers for the active agent (solute) and/or solvents, such as, methylsulfonylmethane, terpene compounds, skin penetration enhancers, glycerylmonolaurate, quaternium cationic surfactants, N,N-dialkyl alkanolamines, such as N,N-diethylethanolamine, steroids, such as dehydroepiandosterone, oily substances, such as eicosapentanoic acid, vitamins, such as A, $D_3$, E, $K_1$.

According to a particular embodiment of the invention the topical, liquid, composition is effective for transdermal delivery of high molecular weight active agent (solute), especially medicaments and other active agents having molecular weights of at least about 350 Daltons (350 D), at delivery rates of greater than about 0.25 milligrams (mg) per square centimeter ($cm^2$) per 24 hours. According to this embodiment, the composition may be formulated as a unit dosage (e.g. one cubic centimeter (1 cc)) containing from about 0.25 to about 1.5 mg of active agent having a molecular weight of at least about 350 D in a carrier in which the active agent is completely dissolved. The carrier includes a solvent system in which the active agent is at least substantially soluble, at least one solvent modifying compound to facilitate transdermal delivery of the active agent and, as necessary, to increase solubility of active agent in the solvent system; and at least one solute (active agent) modifying compound forming a non-covalently bonded complex with the solute. In this embodiment, too, addition of a substance, e.g., Forskolin, for stimulating cAMP production, or substance for stimulating cGMP production, is preferred for its ability to increase the rate of percutaneous absorption of the active agent into and through the stratum corneum (sc) and viable skin (vs).

In one particular aspect the present invention provides a topical formulation for the transdermal delivery of an active agent having a given polarity and dipole moment; the formulation includes:

(A) at least one solvent in which the active agent is soluble or is modified to solubilize the active agent, and which has substantially the same dipole moment as that of the combination of active agent plus solvent system;

(B) at least one solvent modifier having common structural features as that of the active agent and comprising an ethylenically unsaturated polar group containing at least one functional group containing at least one heteroatom selected from the group consisting of oxygen, nitrogen and sulfur;

(C) at least one metabolizable solute modifier comprising a compound capable of forming a temporary (non-covalently bonded) complex with the active agent;

(D) at least one source of cellular activation energy; and, optionally, (E) at least one skin stabilizer for stimulating the body's repair mechanisms in response to transdermal migration of the active agent through the skin.

The present invention also provides, in a specific embodiment, a topical formulation for the transdermal delivery of a medicament (or other active agent) having a given polarity, the formulation including (a) at least one non-aqueous non-toxic solvent selected from the group consisting of lower aliphatic mono- and poly-hydroxy compounds;

(b) limonene or lemon oil;

(c) methylsulfonylmethane;

(d) skin stabilizer comprising at least one compound selected from the group consisting of aliphatic carboxylic acid having from about 8 to about 32 carbon atoms, an ester of said aliphatic carboxylic acid with an aliphatic alcohol having from 1 to about 20 carbon atoms, wherein said ester has a total of from about 9 to about 36 carbon atoms, Vitamin $D_3$, and mixtures thereof;

(e) solute modifier comprising at least one compound selected from the group consisting of 3,3'-thiodipropionic acid, ester thereof, salt thereof, oxindole alkaloid, polyphenolic flavonoid, sugar adduct of a gluconuride, isoflavones, phosphatidyl serine, phosphatidyl choline, vitamin $D_3$ and Vitamin $K_1$, (f) at least one substance which induces in situ generation of cAMP or cGMP.

In accordance with a particularly preferred embodiment of this aspect of the invention the component (f) is, or comprises, forskolin or Colforsin, especially forskolin.

According to still another aspect of the invention there is provided a method for forming a composition for the topical application to the skin of a human or other animal for the transdermal delivery of an active agent of known or predetermined polarity contained in the composition. The method includes the steps of selecting a solvent in which the active agent is at least substantially soluble;

selecting modifying agents for each of the solvent and active agent such that when the active agent is dissolved in a solvent system comprising solvent and modifying agents there will form a complex of at least one modifying agent weakly associated with the active agent through van der Waals forces and/or hydrogen bond affinities; said modifying agents comprising at least one ethylenically unsaturated compound having a polar group and an oxygen, nitrogen and/or sulfur containing functional group, and at least one compound for balancing at least one molecular property characteristic of the solvent system and active agent, said molecular property characteristic being at least one of electrostatic energy, non-bonded energy, polarisability and hydrophobic bonding, and the polarities of the modifying agents are such that the dipole moment of the active agent closely matches the dipole moment of the active agent plus solvent system, and forming the pharmaceutical composition by mixing each of the active agent, solvent and modifying agents.

DETAILED DESCRIPTION OF THE INVENTION AND PREFERRED EMBODIMENTS

The present invention provides a transdermal delivery system which is able to quickly introduce a medicament or other active agent through intact skin or mucous membrane or other viable membrane or external covering of animal, including human, or plant, while minimizing damage and, therefore, minimizing the immune response of the skin or membrane to this introduction/challenge.

While the foregoing and following descriptions are given with respect to transdermal or percutaneous administration of drugs or other classes of active agent through human or animal skin, the principles and compositions disclosed herein are not so limited but will also be generally applicable to administration of a broad spectrum of active agents, including medicines, drugs, pharmacologicals and non-bioactive substances or agricultural chemicals for treating plants, and other viable animal membranes. In this regard, it will also be appreciated by those skilled in the art that certain substances may exert medicinal or pharmacological activity when used at high concentration while at lower concentration and/or for a lower extent of transmigration, e.g., without substantially reaching beyond the viable skin to the vascular or capillary network, will exert only a cosmetic effect or weaker pharmacological activity. It will also be appreciated that certain compounds, for example, quaternary ammonium compounds, may in some cases constitute an active ingredient while in other cases such compounds may be included as modifying agents, skin stabilizing agent or for other functional effect.

Accordingly, the term "active ingredient" or "active agent" or similar term is intended to refer to that ingredient or ingredients in the formulation which is intended to and expected to have a half-life of more than a few minutes (e.g., at least about 2, preferably at least about 5 minutes) after introduction into the body and the only ingredient(s) included to accomplish, in the case of a drug or other medicinal or pharmacological agent, a therapeutic outcome, pharmaceutically, or, in the case of an agricultural agent, an equivalent therapeutic outcome, agriculturally.

Furthermore, unless the context indicates otherwise, terms such as "transdermal" or "skin" should be construed to also include penetration through the outer layer of various plant forms, such as trees, flowering plants, cacti, and the like, including, for example, stems, leaves, shoots and the like.

Rapid introduction of the active agent enables:

minimal immune response or anaphylaxis, and repetitive dosing over the same area of skin over a short term or, if needed, for a longer course of therapy.

In order to accomplish the above and other objectives the delivery system is designed to (1) create a transient modification of those aspects of the solvents and solutes which encounter or trigger the body's defense mechanisms against dermal transmigration and, (2) minimize or offset any damage done by dermal transmigration.

The transient modification (1) is manifested by the formation of a complex between the solute (active agent) and the solvent or solvents and modifying agents or modifiers for the solvent(s) and/or the solute. These complexes are formed as non-chemical true solutions of the solute in solvent wherein the components of the complex are held together through weak association, including van der Waals forces and/or hydrogen bond affinities but, substantially no covalent bonding. Furthermore, the carrier for the solute which includes the solvent(s) and modifying agent(s), as will be described below in further detail, is selected to have common structural elements (e.g., physical and molecular orientation, size, shape, etc. and which may be considered as the "morphological" structure of the compound) which are similar to and compatible with the structural elements (morphology) of the solute (active agent) and otherwise exhibits an affinity for the solute whereby the solute is attracted to and associates with the carrier to form a 3-dimensional structure which may be analogized to a Velcro-type mechanism. That is, the carriers of the transdermal delivery system of this invention are designed for each particular drug or other medicament or active agent which allows the resulting complex of active agent to pass through each of the different layers of the skin's defenses with minimal or no irritation while carrying the active agent in its intact, non-dissociated state. As the complex passes through each layer or layers one or more modifying agents of the complex may be stripped away from the complex, usually by preferentially bonding or reacting with a component or components of the skin layer, but without reacting with or disassociating the active agent. This mechanism thus allows the active agent to reach and be absorbed by or react with its intended target, usually absorption into the vascular or capillary network.

In practice, however, in view of the overall similarities of common structural elements with and among large classes of medicaments, it has been possible to design a standard or stock solution which, with only minor modifications or fine tuning, can be used for many different active agents.

The stock solution will generally include (A) solvent(s); modifying agents including (B) solvent modifier(s); and (C) metabolizable solute modifier(s); (D) source(s) of cellular activation energy; and (E) skin stabilizer(s). Other optional ingredients may also be included, for example, (F) capillary dilator(s); (G) enzyme activator(s). The active agent is mixed with the stock solution, further modified, as necessary, to increase solubility and/or more closely match the molecular properties of the stock solution plus active agent to that of the active agent, taking into account one or more effects of the molecular interactions of molecules in a liquid. Each of these components will now be described in further detail.

It is understood that all ingredients used in the compositions of this invention must, within the applied and recommended dosages, be non-toxic and safe for human use. Also, all amounts, parts and percentages in the following description and appended claims are on a weight basis unless otherwise noted.

(A) Solvents

The solvent is the principal component of the carrier for the active agent and, preferably, is one in which the active agent is soluble or at least substantially soluble or can be made soluble or become more soluble, by addition of one or more solvent modifying agents. As used herein, by "substantially soluble" is meant that the minimum effective dose of the active agent, generally at least about 0.25 mg, preferably at least about 0.5 mg, especially preferably about 1 mg, or more, will dissolve in I cc of the solvent(s) or in 1 cc of a mixture of the solvent(s) with solvent modifying agent(s). Suitable solvents may be selected from any of the solvents normally used for medicaments, cosmetics, nutrients or other active agent to be delivered transdermally.

Preferred solvents include lower alcohols of from about 2 to about 6 carbon atoms, preferably from 2 to 4 carbon atoms and may be monoalcohols, such as, for example, ethanol, isopropanol, sec-butanol, or polyols, such as, for example, ethylene glycol, propylene glycol, butylene glycol, glycerol. Mixtures of solvents may be used. Other solvents, such as ketones, e.g., acetone, methylethyl ketone, ethers, e.g., ethylether, may also be used, in amounts which will be safe and non-toxic in use.

While the solvent system is generally non-aqueous water may be used for water soluble active agents and for those drugs or other active agents which are stable in the presence of and not denigrated by the presence of water. Water may also be introduced as a component of one of the other ingredients, for example, as an alcohol:water azeotrope, etc. When water is present in the solvent it will usually constitute less than about 50 percent, preferably less than about 10 percent, especially, preferably, less than about 2 percent, by weight of the total solvent although more or less may be used depending on the active agent and so long as the objectives of the invention can be met. Furthermore, as will become apparent by the examples to follow, the compositions of this invention and utilizing the principles which will be described in more detail, hereinafter, may also be formulated as aqueous emulsions, including wherein the aqueous phase is the major and continuous phase. Such aqueous emulsions, as is the case with non-aqueous (usually less than about 5%, especially less than about 2%, of water) solvent systems, will be rapidly absorbed by and release the active agent or agents in, typically, less than one minute.

Generally, the total amount of solvent(s) will be selected to assure dissolution of the solute and other additives and provide suitable product viscosity. Generally, the amount of solvent(s) falling within the range of from about 5 to about 90 percent, preferably from about 25 to about 75 percent, based on the total composition, may be used.

(B) Solvent Modifiers

A solvent modifier is selected to modify the polarity of the solvent system to closely match that of the active ingredient (solute). Therefore, solvent modifiers will usually be polar compounds (form polar ions in solution) and will usually contain a functional group containing oxygen, sulfur or nitrogen in its molecule. Also, if the active agent is unsaturated the solvent modifier will usually also contain double bonds in the straight-chain or cyclic portion to match the structure of the active agent. Most importantly, the solvent modifier or mixture of solvent modifiers enables the solvent system [solvent(s) and solvent modifier(s)] to form a weak complex with the active agent, i.e., an association via van der Waals forces and/or hydrogen bonding, thus yielding a stable composition with a high solute/solvent ratio. As used herein, "stable" is intended to have its normal and usual meaning, namely, that the composition may be stored at room or elevated temperature for one or more days, usually 30 or more days, without undergoing phase separation. By "high solute/solvent" ratio is meant at least 0.25 mg solute per cubic centimeter of solvent (or solvent plus modifying agents) and, more generally, often amounts of solute exceeding the solubility of the solute in the solvent alone, or in each solvent of a multi-solvent system.

As noted above, solvent modifiers may be individually (or as a group) selected from substances having structural elements in common with the active agent. However, it has been found that for many bio-active compounds and other active agents, a relatively small group of solvent modifiers facilitate the dissolution of the active agent and formation of the weak association which enable the complex of active agent-modifier to pass the defenses of the skin with minimal irritation without modification of the chemical structure or stereoscopic configuration of the active agent.

Thus, particularly favorable results have been obtained by using as the solvent modifier one or more of lemon oil (or/and d-limonene), Vitamin E, Pro-Vitamin B, D-panthenol and methylsulfonylmethane (MSM).

The amount of solvent modifier will be selected to result in the desired solute/solvent ratio, and will depend on various factors, including, for example, primarily, the polarities, and polarizabilities, dipole moments, van der Waals forces of each component, including the solvent, solvent modifier and solute (active agent).

In this regard, in order to match the polarities, dipole moments, of the solute to that of the solvent system the amount of the individual components of the solvent system will be selected such that the weighted (molar) average of the dipole moments of the individual components will be substantially the same as the dipole moment of the solute in solution.

Generally, the suitable amount of solvent modifier(s) to achieve the desired solute/solvent ratio will fall within the range of from about 0.0001 to about 50%, preferably, from about 0.1 to about 35%, more preferably, from about 0.1 to about 5%, based on the total composition.

(C) Solute Modifiers

The solute modifier may be included in the formulation of the topical delivery system where necessary to facilitate dissolution of insoluble or sparingly soluble solutes at higher concentrations. Solute modifiers which form reversible or temporary complexes with the solute to facilitate passage through the skin while minimizing immunological response are especially effective. The solute modifier will also, optimally, be a nutritional compound which will be metabolized by the body once the solute is released from the complex.

Examples of preferred solute modifiers include, for example, terpenes, such as, for example, *Uncaria Tomentosa* ("Cat's Claw"), oxindolealkaloids, quercitrin (glycoside of quercitin), genistein and its glucoside, genistin, polyphenolic flavinoids, such as found in concentrated grape seed extracts, scutellarein and other sugar adduct gluconurides, such as, scutellarin, trans-ferulic acid, alpha-lipolic acid, sterols, such as, for example, cholesterol and cholesterol-like compounds and hormones, such as isoflavones, 3,3'-thiodipropionic acid (sulfurated propionic acid), phosphatidyl serine and choline, Vitamin $D_3$, Vitamin $K_1$, dehydroepiandosterone (DHEA). Still other suitable candidate compounds include, for example, berberine, piper nigrum (e.g., ioperin®), phosphatidyl serine, phosphatidyl choline. Another group of candidate compounds include boswellic acid, hypericum, phytic acid.

The selection of the particular complexer will facilitate movement of the solute-complex past the stratum corneum and viable skin to its optimal targeted internal circulation system of blood, lymph or neural; or past the vascular system, to anchor the bio-active agent, if so desired, deep in the tissues.

The suitable amount of the solute modifier may be determined based on such factors as, for example, solubility of the modifier in the system (e.g. solvent plus solvent modifiers), its molecular compatibility with the solute, its ability to modify the polarizability of the solute to increase the concentration (solubility) of solute in the solvent, etc. Generally, the amount of solute modifier will be at least about 0.003%, such as, for example, from about 0.003 to about 5%, preferably from about 0.1 to about 5%, especially preferably from about 0.1 to about 4%, based on the weight of total composition. Furthermore, it is especially preferred that the amount of solute modifier or modifiers is equivalent to the amount of solute to provide a 1:1 interaction between modifier(s):solute.

In general, the above described modifying agents, i.e., solvent and solute modifiers, as well as other components of the solvent/carrier delivery system of this invention should preferably be selected from substances which the body recognizes as usable building blocks of other physiological systems. This selection therefore facilitates nearly complete disassociation of the medicament from the delivery system once in the body. Since these carrier/complex compounds are reducible to elemental building blocks of physiology they should do no harm to the body.

(D) Source of Cellular Activation Energy

The process by which transdermal drug delivery operates involves moving molecules across chemical and electrical gradients. Under ordinary tonic conditions, the introduction of materials through the skin results in chemical cascades that consume relatively large amounts of energy as the body seeks to defend itself against the challenge. Therefore, the topical transdermal delivery system of the present invention, according to one preferred embodiment, includes a substance which brings stored energy or the stimulus for release of stored energy on a cellular level, thereby minimizing energy-negative reactions, which could lead to sensitization, ACD or anaphylaxis. By including such stored energy substance, there is a multiplied net increase in available cellular energy and, accordingly, the potential acceleration of those reactions which result in the active agent ultimately reaching its target and being effectively utilized by the body.

While the composition may be formulated to utilize adenosine diphosphate (ADP) or nicotinamide adenine dinucleotide (reduced form) (NADH) or flavin adenine dinucleotide (reduced form) ($FADH_2$), such compounds tend to be unstable and, therefore, are often not preferred.

There has been identified a group of botanical compounds which, due, apparently, to so-called signalling mechanisms, induce high concentrations of enzyme-substrate complexes to be formed, such as by activation of the N, (stimulatory) protein of adenylate cyclase, thereby resulting in cellular levels of adenosine 3',5'-cyclic monophosphate (cAMP) approaching the maximal limits of cellular cAMP concentration.

In particular, extracts of the plant *Coleus Forskholi*, and especially, Forskolin, a labdane diterpenoid, have been found to have a particular ability to stimulate the production of cAMP in cells (Refs. 14 and 15). Other extracts of *Coleus Forskohli*, such as, Colforsin or coleonol, for example, may also be used.

Other examples of activation energy sources for stimulating generation of cAMP, either via precursors or cellular activators, include, for example, methyl xanthines, Saikogenin and Saikosaponin, *Angelacie dahuricae* radix (yielding angelic acid), phelopterin, oxypeucedanin.

Examples of substances which stimulate cellular production of cGMP include acetylcholine, cytidene diphosphocholine and ascorbic acid (vitamin C).

The amount of the activation energy source will depend on such factors as, for example, the mechanism of action of the active agent, energy of activation (positive or negative) when active agent encounters its intended receptor (to enhance or decrease cAMP or cGMP levels), etc. Generally, suitable amounts of forskolin or acetylcholine or other source of cellular activation energy, will fall within the range of from about 0.001 to about 0.1%, preferably, from about 0.001 to about 0.01%, more preferably, from about 0.001 to about 0.005%, based on total composition. As will be appreciated by those skilled in the art, cGMP is considered an antagonist for cAMP. cGMP stimulation will generally be appropriate for situations where it is desired to enhance immune function, such as lymphocyte mediated cytotoxicity, during infection, carcinogenesis, etc. Conversely, cAMP stimulation is generally appropriate in situations where immune system modulation is desired.

(E) Skin Stabilizers

Skin stabilizers may be included in the compositions of this invention to stabilize the skin prior to passage and to assist the skin to repair any damage resulting from the transmigration of the active agent and solvent and other components of the formulations.

Suitable skin stabilizers may provide one or more of the following attributes to facilitate safe and effective dosing of the active agent while avoiding local or systemic sensitization: form hydrogen bonds and complex with free radicals; act as a bridge for collagen, keeping the strand intact temporarily during repair; stimulate the body's repair mechanisms, modulating prostaglandins, cytokines and the like; re-stabilize the Elastin complex after the composition passes through the skin; carry cationic potential, stimulating nerve transmission, i.e., decreasing nerve repolarization time at synapses. In addition, preferred skin stabilizers should be able to be metabolized by the body and should also shield the medicament or other active agent from the skin's defense mechanisms by forming suitable complexes which will be readily uncomplexed when the active agent reaches its intended site.

Examples of substances which may function as skin stabilizers and which may be included in the compositions of this invention include glycerin monolaurate (e.g., as Lauricidin®) and similar fatty acid esters, Vitamin $D_3$, alkoxy glycerols, unsaturated fatty acids, such as, eicosapentaenoic acid (EPA), docosahexaenoic acid (DHA), and gamma-linolenic acid (GLA), Vitamin E (alpha tocopherol) and the esters, e.g., acetate, and derivatives thereof, e.g., tocotrienol, D-panthenol, phytantriol, dehydroepiandosterone (DHEA), pregnenolone, pregnenolone acetate, esculin, allantoin, ascorbyl palmitate, and the like.

Suitable amounts of the skin stabilizers may be determined based on such factors as, for example, type of reaction between drug (active agent) and skin, between solvent and skin, etc. Generally, amounts of skin stabilizer, when present, will be at least about 0.01%, such as, for example, from about 0.05 to about 5%, preferably, from about 0.1 to about 5%, more preferably, from about 0.1 to about 2%, by weight, based on total composition. It is preferred to select stabilizers which will be effective in stabilizing the skin at as low a concentration as possible.

(F) Other Ingredients (i). Membrane Permeability Modifiers.

In order to further enhance the ability of the solute to reach its cellular target the compositions of this invention may optionally include substances which have the ability to provide a transitory effect on membrane permeability. Many such substances are described in the general and patent literature and are often referred to as skin penetration enhancers, percutaneous absorption enhancers and similar terms. For instance, the fatty acid esters, alkoxy glycerols, allantoin, ascorbyl palmitate, and unsaturated fatty acids mentioned above as skin stabilizers may also sometime be effective to temporarily enhance cell membrane permeability.

Other useful membrane permeability enhancers which have a transitory effect include, for example, Quaternium 28, Quaternium 18, and other cationic quaternary ammonium compound surfactants or emulsifiers, sulforaphen, cineol terpinen-4-ol, N,N'-diethyl ethanolamine, N,N'-dimethyl ethanolamine, and the like.

When used, amounts of the membrane permeability modifiers may range from about 0.01 to about 5%, preferably, from about 0.01 to about 4%, more preferably, from about 0.05 to about 2%, based on the weight of total composition.

(ii). Enzyme Activators/Signalling Compounds

Substances which function as signalling agents, namely, to provide a signal to the target cell or tissue but without crossing the cellular boundary either intact or as fragment but which facilitate the uptake of medicaments or other bio-active agents, such as by stimulating a particular intercellular response, may also be included in the subject compositions.

In particular, mention may be made of substances which modulate enzyme-substrate (ES) complexes to change the velocity of reactions and the resulting kinetic energy, such as, for example, the relative saturation of the enzyme by the substrate. In addition to the above mentioned functions, Forskolin, sulforaphen and sulforaphane are believed to function as such enzyme activators/signalling compounds, by acting as catalysts for the ES reaction, thereby yielding more rapid orientation of ES complexes to cellular receptors. (see, e.g. Ref. 13, Chapter II, pages 235–253).

Suitable amounts of such enzyme activators/signalling compounds will usually be in the range of from about 0.01 to about 0.05%, preferably, from about 0.01 to about 0.02%, by weight, based on the total composition.

(iii). Capillary Dilators

Compounds which function as capillary dilators may also be included in the subject formulations to facilitate passage of the active agent-complex through the skin and/or provide additional capillary surface area to facilitate uptake of the active agent into the vascular system. Compounds which may be incorporated to function as capillary dilators should be of low toxicity and readily reversible; suitable compounds include, for example, in addition to known vasodilators, saponins, Quaternium 28, and sulforaphen. Preferred compounds should be able to sequentially open and close ("unzip/zip") the hydrogen bonds in hyaluronic acid (HA) of elastin as the complexed active agent passes through the skin.

Suitable amounts of capillary dilator, when present, may range from about 0.1 to about 2%, preferably, from about 0.1 to about 1.5%, by weight, based on the total composition.

Formulations

In formulating a carrier system of solvent, modifying agents, including solvent modifier and solute modifier, and other components, for the transdermal delivery system of this invention, several factors may be considered in selecting the particular ingredients to be included. For example, such factors as (1) the availability of pure drug versus a salt of the drug; (2) the solubility of the active agent (usually solubility of a solute in a solvent may be predicted by the relative dipole moments, the closer in value the more soluble will be the solute); (3) whether or not an ingredient will form an adduct or otherwise react with or degrade the solute or the complex of solute-solvent; (4) common structural features and physical characteristics of solute and solvent; (5) hydrophilic/lipophilic balance (for non-polar solutes) (6) pH (should be matched to that of the active agent, generally in the range of from about 2.5 to about 8.0, preferably 3.0 to 6.0, especially from about 3 to 4, especially for acidic active agents and/or to minimize or relieve pain on the exposed skin where the composition is applied; pH may be increased or decreased depending on the active agent, e.g., to prevent ionization or salting out effects; the compositions may often be formulated to be self-buffering but, if necessary, pH may be adjusted by addition of appropriate acids or bases, or by addition, for example, of quaternary compounds, ethylene diamine tetraacetic acid, or the like).

The topical transdermal delivery system of this invention is preferably in the form of a lotion or similar free flowing liquid (e.g., solution, emulsion, etc.). Due to the very rapid absorption and uptake of the active agent the lotion may be directly applied to the skin without accommodating for product runoff. For example, in most cases the formulation is rapidly absorbed into the skin within a few to several seconds after application and with a high (e.g. >90%) percentage of the active agent being transmigrated and made bio-available.

However, if desired, various additives, such as thickeners or gelling agents may be incorporated to form gels or creams according to standard pharmacological and cosmetic technology. Alternatively, the topical transdermal composition may also be incorporated into a TDD system, e.g., patch. However, in all of these modified forms it is expected that the efficiency of delivery will be impaired with regard to rate of absorption and amount of active agent delivered. Therefore, it is generally preferred to exclude gelling or thickening agents and to apply the formulation as a liquid (lotion) directly to the skin rather than as a component of a patch system or directly as a gel.

A standardized or Stock Delivery System (SDS) for the solvent/carrier delivery system which has been found to be effective for a wide range of drugs and other active agents is set forth below. In the following table the "amount" of each ingredient is on the basis of an approximately 2 liter system. The amount of the active ingredient or ingredients which may be incorporated into the SDS will depend on the nature of the active ingredient, but generally may range from about 0.1 gram to about 100 grams, preferably from about 0.1 to about 60 grams per liter of SDS, more preferably, at least about 0.25 gram, especially at least about 0.5 gram, such as from about 1 to about 45 grams or more, per liter of SDS, corresponding to a 1 cc unit dosage of from about 0.1 to 100 mg, preferably from about 0.1 to 60 mg, more preferably at least about 0.25 mg, especially at least about 0.5 mg, most especially at least about 1 mg, per cubic centimeter (cc). These ranges apply for both biological (e.g., drug) and non-biological (e.g., cosmetic) active ingredients.

| Compound | Function | Amount broad | Amount intermediate | specific units |
|---|---|---|---|---|
| Ethanol, i-propanol, or sec-butanol | solvent | 1000–1200 | 1050–1150 | 1125 cc |
| Propylene glycol | solvent | 700–900 | 750–850 | 800 cc |
| Natural Lemon Oil | solvent modifier | 1–3 | 1.5–2.5 | 2.0 g |
| D-Panthenol | solvent modifier | 0.5–1.5 | 0.7–1.2 | 1.0 g |
| Methyl sulfonyl methane | solvent modifier | 1–3 | 1.5–2.5 | 2.0 g |
| Glycerol Monolaurate | skin desensitizer | 2–10 | 3–8 | 5.0 g |
| Vitamin $D_3$ | skin stabilizer | 0.01–0.5 | 0.04–0.25 | 0.1 cc |
| Uncaria Tormentosa (15% polyphenols) (3% oxindoles) | solute modifier | 1–3 | 1.2–2.5 | 2.0 g |
| 3,3'-Thiodipropionic acid | solute modifier | 0.5–2 | 0.7–1.6 | 1.0 g |
| Forskolin (pure) or | Source of ATP | 0.01–1 | 0.02–0.6 | 0.1 g |
| Forskolin (extract 40%) | | 0.1–2.5 | 0.1–1.4 | 1.0 g |

The above Stock Delivery System may be modified, generally, as a first approximation, as a function of the polarity of the active agent. Where the solute is soluble in the alcohol/glycol solvents at the desired level no further solvent modification, as such, may be required. However, it is often preferable in such case to modify the system to allow even higher dissolved solute concentrations so that smaller unit dose or less frequent applications are feasible.

In this regard, it is understood that the dipole moment of a given compound may be taken directly from the literature, when available, or otherwise measured or calculated by standard techniques, including commercially available chemical modeling software packages. Generally, dipole moment is experimentally determined for an element or compound by suspending a molecule in an electromagnetic field and measuring the amount of energy (torque) to rotate the molecule one rotation. Dipole moment is correlated to van der Waals forces and the number of hydrogen bonds as well as electrostatic energy of a molecule. Two chemical entities with approximately the same dipole moment will usually have an affinity for and be attracted to one another without the necessity for covalent bonding.

To determine the dipole moment of the solvent(s) and modifiers, a weighted average of the-dipole moments of the individual components is used. The weighted average should closely approximate the dipole moment of the solute. The closer the match the faster will be the rate of transmigration through the skin. Generally, the Stock Delivery System will be modified, as necessary, to move the dipole moment of the solvent solution with modifying agents and other additives, including the solute, to as close as possible to that of the solute, preferably within 15%, especially within 10%, most especially within 5%, of the dipole moment of the solute.

More specifically, in accordance with the preferred method for forming the compositions of this invention, especially for increasing the amount of drug or other active ingredient which can be stably carried in solution in the inventive transdermal delivery compositions, the selection of and the amounts of the ingredients of the solvent system and other functional additives may be determined, in the first instance, by balancing the dipole moment of the active agent relative to the dipole moment of the final composition. The dipole moment of the final composition is taken to be the weighted average dipole moments of each individual ingredient. The weighted average is obtained by calculating the sum of the mole-moments of each ingredient, where the mole-moment is obtained by mutiplying the amount, in moles, of an ingredient, in a given volume, e.g., 100 cc, by the dipole moment for that ingredient. For purpose of this calculation it is assumed that each ingredient in the composition acts independently of the other ingredients. Thus, for example, the dipole moment of any particular ingredient does not take into account the electronic, e.g., repulsive or attractive, effects of other ingredients. However, by taking concentrations into consideration, that is, by multiplying individual dipole moments by molar concentrations, a reasonable approximation of the matching of the system's properties with that of the solute will generally be achieved.

As will be described further below, closer and more accurate matching or fine-tuning of the solute and delivery system may be achieved by taking other molecular characteristics into consideration.

It is also understood that for the above Stock Delivery System, the stated amounts may be varied, for example, by as much as about ±2.5% or more, depending on the particular active agent, and the desired degree of matching of dipole moments, and/or, other molecular properties, particular van der Waals forces, as discussed above and below. One or more of the compounds listed above may be omitted or replaced by a functionally equivalent compound. Some of the ingredients may also provide functions in addition to those stated in the table.

For example, glycerol monolaurate, commercially available under the tradename, Lauricidin®, may be replaced, in whole, or in part, by other long chain fatty acids or esters. 3,3'-Thiodipropionic acid is primarily effective to promote delivery of amino acids, glycosides and sugars and, for other types of active agents, may be omitted, or replaced with other propionic acid derivatives. Similarly, Uncaria Tormentosa (Cat's Claw) is primarily effective in delivery systems for primary alkaloid and terpenoid active agents, and may be replaced with similar terpenoids, oxindolealkaloids, polyphenolic flavinoids, etc. Vitamin $D_3$ also functions to sweep toxins and enhances Na/K and Mg/Ca pumps.

In addition to the above ingredients the Stock Delivery System may also include, for example, phytantriol which has a similar function to d-panthenol, namely, as a solvent modifier and for its ability to facilitate refraction from hyaluronic acid (HA) in skin. When added to the stock formulation its typical amount is about 1.0 g (per 2 liters).

Dehydroepiandosterone (DHEA) is another highly useful solute modifier. When incorporated in or added to the SDS it is usually effective in amounts of about 100 mg (per 2 liters). Other optional, but often useful components which may be included in or added to the above SDS include, oily substances, for example, conjugated linoleic acid (CLA), medium chain (e.g. $C_6$–$C_8$) mono-, di-, or tri-glycerides, olive oil, Emu Oil, or Melaleuca Oil (preferably 100% purity) to increase the saturation point of the system but without facilitating supersaturation; N,N-diethylethanolamine or N,N-dimethylethanolamine, effective for modifying dipole moment and aiding in complexing of solute to modifiers, as well as a skin penetration enhancer; pregnenolone or pregnenolone acetate, as a drug complexer and/or for increasing transdermal migration and/or skin stabilization; transferulic acid or alpha lipolic acid, as antioxidants and for controlling the re-complexing of the HA in elastin and skin, also functioning as a solute complexer; Berberine, as a signalling mechanism for enhancing more efficient uptake of certain medicaments by cells.

It is understood that the above are only exemplary of suitable additives and modifications to the transdermal delivery systems of the invention and that other additions, deletions or modifications can be made within the guidelines provided herein and by the more detailed examples to follow.

While the Stock Delivery System as above or appropriately modified for the particular active agent of interest will usually be formulated in large size batches the compositions of this invention including the active agent will often preferably be provided for dispensing in unit dosage forms, as well known in the art. For example, individual sealed packages or metered dosage pump type containers for dosing about 1 cc of composition, may be provided to contain sufficient active agent for a single application.

Laminar matrix transdermal systems are designed to leech medicament through the stratum corneum into the dermis and the vicinity of the cutaneous plexi of the capillaries. This is a slow process, usually requiring hours to days to deliver the maximum available dose. Since deep penetration is generally not possible for these systems without external iontophoretic accelerators, they are limited to delivery of medicaments which are systemically efficacious in relatively small doses, and generally only deliver one third of the drugs with which they are loaded.

In contrast, the transdermal delivery system of this invention can effectively deliver at least about 90% or more of the medicament rapidly through the skin to the underlying fatty tissue. This delivery may be accomplished in only a few to several tens of seconds or just a few minutes or less. In some cases, it may be desirable to slow down the rate of trans-migration, for example, to direct the dose of the medicament for systemic administration via the capillary net of the dermis. Particular medicaments for which systemic administration is often indicated include, for example, hormones, vitamins, systemic antibiotics.

Such slowing down may be accomplished by modifying the stock delivery system so that there is mismatching of the dipole moments of the solute and the solvent(s) and modifying agent(s), for example, at least about 15% or more difference, such as about 15 to about 35% variation, especially from about 20 to 30% variation. By so varying the dipole moments and/or other molecular characteristics, of the solute and the SDS for the solute a more shallow penetration of the solute and/or a less acute uptake curve may be achieved. Here too, however, the resulting complex of the solute with the SDS components will effectively shield the medicament (active agent, solute) from the body's defenses, yet will not "slip" through quite as effectively or efficiently. This dipole moment mismatching, may therefore, be effectively utilized to insure that, at any given time, more medicament is in the general vicinity of the cutaneous plexi and available to be picked up by the capillary network for systemic delivery.

In the case of therapy requiring slower delivery, the system may be balanced to take longer to get to the strata of the target, by emphasizing lipophilic binding affinities in the solute modifiers. Some medicaments may safely be moved past the cutaneous plexi and stored in the fascia beneath the capillary net. This level is not as well defined by cell-mediated immune response and may serve as a natural storage and release matrix for delivery of these medicaments.

Slower transmigration and/or bioavailability may also often be achieved, for example, by modifying the hydrophilic-lipophilic balance (HLB) of solute modifiers and/or by "shielding" the medicament with lipids which will increase the time to de-complexing of the solute-modifying agent complex.

While the above discussion focuses on the matching of the dipole moment of the active agent with the SDS, e.g., solvent(s), solvent modifier(s) and solute modifiers), and will allow one skilled in the art to effectively formulate topical delivery systems according to the invention, still further refinements, and improved consistency, may be obtained by further taking into consideration other parameters which are characteristic of the physicochemical properties of the solute (active ingredient, e.g., drug) and the carrier components of the topical delivery system. In particular, the following properties of the solute and the delivery or carrier system can be measured or calculated or may, in some cases be obtained directly from the published literature: entropy, enthalpy, Free energy, Potential energy, Kinetic Energy, Dipole Moment, Surface Interaction parameters. Matching these various parameters between the solute and the delivery system will facilitate the transdermal delivery of the solute to the intended target.

More particularly, the following is a more specific overview of how the solvents, modifying agents and other enhancing agents and additives may be compounded together to standard stock delivery carrier system and how any particular medicament molecule (or other active agent) is evaluated and the delivery system consequently modified to maximize solubility and optimize transmigration to the target level of skin or tissue.

Many molecular properties come into play with molecules in close proximity. A representative list of these includes steric energy, heat of formation, dipole moment, charge density, non-bonded energy, COSMO salvation in water, electrostatic potential, electron spin density, hyperfine coupling constants, atomic charges, polarisability and others such as IR vibrational frequencies. According to the present invention, the molecular evaluation system is particularly concerned with 4 of the several forces in play on the molecules of the system and the medicament. These four elements are:

Electrostatic Energy

Non-bonded Energy

Polarisability

Hydrophobic Bonding

These four elements constitute a graded, increasingly fine approximation to balance of those factors and vectors which are predictive of dissolving a particular medicament in a liquid medium, the aggregation of which is designed to rapidly transmigrate the lipid domains of the SC by means of temporary disruption, continue traverse through the VS to the capillary plexi beneath or past the plexi into the fascia lata or deeper as required, the entire process being accomplished so as to assist in repair of damage secondary to domain modulation and minimization of hapten formation and any subsequent cascade.

Electrostatic Energy

The Electrostatic energy which is the first parameter of intermolecular forces which may be controlled can be described with the equation:

$$E_{Electrostatic} = \sum_{i}\sum_{j} \frac{q_i q_j}{D r_{ij}}$$

where the Electrostatic energy is a function of the charge on non-bonded atoms, q; their inter-atomic distances, $r_{ij}$ and a molecular dielectric expression, D, which accounts for the attenuation of electrostatic interaction by the environment, e.g. between the solvent and solute modifiers and between the system and the medicament itself.

In a preferred embodiment, the electrostatic energy may be modelled by the Chem3D software, available from Cambridge Soft Corporation, Cambridge, Mass., using atomic charges for charged molecules and bond dipoles for neutral molecules. There are three interactions which are accounted for through the Chem3D software. These include Charge/Charge interactions; Dipole/Dipole interactions; and Dipole/Charge interactions. These interactions are calculated for each molecule of the carrier system and the medicament separately and then a weighted molar average calculation accounts for the system as a whole, and this quotient is balanced against the medicament as to gross order of magnitude. Each type of interaction uses a different form as shown below:

$$E = 332 \cdot \sum_{i}\sum_{j} \frac{q_i q_j}{D_q r_{ij}}$$

where the value 332 converts the results to units of kcal/mole.

Dipole/dipole contribution:

$$E = 14.4 \sum_{i}\sum_{j} \frac{\mu_i \mu_j}{D_\mu r_{ij}} (\cos - 3\cos\alpha_i \cos\alpha_j)$$

where the value 14.4 converts the result from ergs/mole to kcal/mole, is the angle between the two dipoles, $\mu_i$ and $\mu_i$, $\alpha_i$ and $\alpha_j$, are the angles which the dipoles form with the vector $r_{ij}$, connecting the two at their midpoints, and $D_\mu$ is the effective dielectric constant.

$$E = 69.1 \sum_{i}\sum_{j} \frac{q_i \mu_j}{r^2 ij \sqrt{D_\mu D_q}} (\cos\alpha_j)$$

where the value 69.1 converts the results to units of kcal/mole.

Bond dipole parameters, $\mu$, for each atom pair are stored in bond stretching parameter table of the Chem3D software or may be obtained from the literature or other available databases, such as, for example, Cambridge Structure Database, or experimentally. The charge q is stored in the Molecular Mechanics (MM2) atom types table. The molecular dielectric is set to a constant value between 1.0 and 5.0 in the MM2 Atom types table.

Non-bonded Energy

The second parameter which may be manipulated and balanced is Non-bonded Energy. Molecular mechanics describes the energy of a molecule in terms of a classically derived potential energy functions and the parameters used for their evaluation are known as "force field" parameters. Molecular mechanical methods are based on the following principles:

Nuclei and electrons are lumped together and treated as unified atom-like particles.

Atom-like particles are regarded as spheres.

Bonds between particles are viewed as harmonic oscillators and therefore subject to principles of harmonic conservation of energy.

Non-bonded interactions between these particles are treated using potential functions derived from classical mechanics.

Individual potential functions are used to describe the different interactions; including bond stretching, angle bending, torsional or bond-twisting energies and non-bonded or through-space interactions (the interactions of most concern in the subject liquid system)

Potential energy functions rely on empirically derived parameters, e.g., force constants, equilibrium values, that describe the interactions between sets of atoms.

The sum of interactions determine the spatial distribution or conformation of atom-like particles.

Molecular mechanical energies have no meaning as absolute quantities. They can only be used to compare relative steric energies between two or more conformations of the same molecule.

Molecular theory typically treats atoms as spheres and bonds as springs. The mathematics of spring deformation (Hooke's Law) is used to describe the ability of bonds to stretch, bend and twist. Non-bonded atoms defined as greater than two atoms apart, interact through van der Waals attraction, steric repulsion, and electrostatic attraction/repulsion described above. These properties are easiest to describe mathematically when atoms are assumed to be spheres of characteristic equal radii.

The total potential energy, $E_{TP}$, of a molecule can be described by the following summation:

$$E_{TP}=E_S+E_B+E_T+E_{NBI}$$

where $E_S$ is Stretching Energy, $E_B$ is Bending Energy, $E_T$ is Torsion Energy and $E_{NBI}$ is Non-bonded Interaction Energy. The first three terms are the so-called bonded interactions. In general, these bonding interactions can be viewed as a strain energy imposed by a model moving from some ideal zero-strain conformation. The last terms, which represents non-bonded interactions, is the variable which is of most concern for the present liquid compositions.

The non-bonded energy represents the pairwise sum of the energies of all possible interacting, non-bonded atoms i and j with a pre-determined "cut-off" distance. The non-bonded energy accounts for repulsive forces experienced between atoms at close proximities, defined as less than 2 Å and for the attractive forces felt at longer distances, defined as greater than 2 uniform molecular radii. It also accounts for their rapid fall-off as the interacting atoms move farther apart by a few Angstroms.

Repulsive forces dominate when the distance between interacting atoms becomes less than the sum of their contact radii. This repulsion can be modelled by the following equation which combines an exponential repulsion with an attractive dispersion interaction ($1/R^6$):

$$E_{van\ der\ Waals}=\Sigma_i\Sigma_j\epsilon(290{,}000e^{-12.5/R}-2.25R^{-6})$$

where $$R=\frac{r_{ij}}{R_i^*+R_j^*}$$

where $R_i^*$ and $R_j^*$ are the van der Waals (VDW) radii of the atoms, epsilon ($\epsilon$) is the depth of attractive potential energy and consequent relative ease with atoms can be pushed together and $r_{ij}$ is the actual distance between the atoms.

At short distance, the above equation favors repulsive over dispersive interactions. To compensate for this at short distance ($R\leq 3.331$ Å) this term is replaced with:

$$E_{van\ der\ Waals}=336.2\Sigma_i\Sigma_j\epsilon R^{-2}$$

For certain interactions, values in the VDW interactions parameter table of the ChemPro 3D software package are used instead of those in the MM2 atom types table. These situations include interactions where one of the atoms is very electronegative relative to the other, such as in the case of water.

Polarisability

The third parameter allowing for modulation towards the balance of medicament and carrier system is polarisation. Polarisability values are calculated by Chem3D software using the following equations. Of special concern is the orientation polarisation ($P_d$) caused by the preferential alignment of permanent dipoles in the direction of the electrical, or in this case, the bio-electrical field. To compute $P_d$, the magnitude of the dipole moment M induced in a molecule by the field acting on it must be factored in. It is assumed that this induced moment is proportional to the strength of the field F, so that:

$$m=\alpha F$$

The proportionality factor $\alpha$ is called "polarisability." It is the induced moment per unit of field strength. Note that $\alpha$ has the dimensions of volume since:

$$\frac{Qr}{(Q/r^2)}=r^3$$

The polarisability of a hydrogen atom is 4.5 $a^3$, which is close to the volume of a sphere of radius equal to that of the Bohr orbit, $4/3\pi a^3{}_0=4.19\ a^3{}_0$. The polarisability of an atom is a good measure of its volume.

If the dielectric is not a gas, as is the case with the present liquid compositions, the influence of the surrounding molecules has to be accounted for in order to estimate the field that acts to polarise a given molecule or atom-like particle. For gases at high temperatures, for non-polar liquids, and for dilute solutions of polar solutes in non-polar solvents, the effective field F is often taken to be:

$$F=E+\frac{4\pi}{3}P$$

It follows then that $$m=\alpha E+\frac{4\pi}{3}P$$

from which is obtained $$P_m=\frac{\epsilon-1M}{\epsilon+2p}=\frac{4\pi L\alpha}{3}$$

where $$P\left(=\frac{3}{4\pi}(F-E)\right)$$

is the polarisation of individual molecules, E is eletrical energy and Pm is called the molar polarisation.

Polarisation is a calculation in the X, Y, and Z planes and then averaged for each molecular constituent of the carrier and then for the carrier versus the medicament. Bond stretch parameters are not considered. The carrier and medicament are viewed as Atom-like particles. For the same reason energies of vibration and libration defined above, may be ignored.

Hydrophobic Bonding

The fourth and finest refinement of the balance is accomplished by modulating Hydrophobic Bonding. These parameters are calculated from the average potential of each Hydrogen atom on each specific constituent molecule. This last factor becomes particularly important in hydrophobic lipophilic systems and is obviously critical in protein delivery, since ethylated fatty acids replace alcohol or propylene glycol as the primary solvent for the system. This averaged value can be seen as the capacity of the carrier for low polarity, lipid solubility and compares the potential of the Hydrogen molecules on the outer surface of the solvent and solute. Hydrophobic Bonding values may be calculated by Chem3D software.

In practice, a data base on the primary, secondary, and tertiary ingredients of a standard delivery system as well as alternate solvents and modifiers for medicaments requiring a different approach such as proteins or very large polymerized molecules will be established. By "primary," "secondary" and "tertiary" is meant ingredients which exert major or gross changes in system properties, e.g. dipole moments, van der Waals forces, etc. (primary); ingredients which make only small changes in system properties (secondary) and ingredients which can be used for "fine-tuning" the system properties to match the properties of the solute (tertiary).

The following tables are typical data sheets generated by the Chem3D software. These charts confirm the independent experimental solubility data and also, in Tables 1–3, show how modulation of the carrier system allows a higher dose of the test medicament, Diosgenin (MW=414.61). Table I shows balance (and maximum solubility) at 0.25 grams in a typical Stock Delivery System (SDS) according to the invention; Table 2 shows that modulating the system by adding isopropyl alcohol increased the solubilized dose to 1.2 grams, a nearly 5-fold increase. Table 3 shows that when the van der Waals forces of the delivery system with and without drug are mismatched, the system becomes unstable, namely, the solubility limit of the drug is exceeded and a precipitate forms when the composition is allowed to stand overnight.

It is pointed out, however, that the formulations shown in the following Tables, and which are based on the above described Stock Delivery System, were originally prepared without benefit of the use of the Chem 3D software and included omission of several different modifiers. Modifications to the SDS to effect solubilization and increase solute solvent ratios were made by the inventor on the basis of knowledge of how and where the solute (drug) works in the body and using this information to make intuitive predictions of how the solute would interact with the surrounding molecules of the SDS, such as induced polarities relative to other molecules; induction of electric fields due to influence of surrounding molecules; hydrophobic versus hydrophilic properties, etc., while always taking into consideration the desired functional effects contributed by each ingredient. Thus, it should be understood that these tables provide a more rationalized basis and unifying theory of the operation of the invention and should allow for preparing stable compositions containing different solutes at high solute/solvent system ratios. For example, using computer modelling of chemical structure can often facilitate understanding of polarizabilities and possible interactions between the drug and other potential components of the system. Again, any potential component must be compatible with the active agent, namely, not form or induce a chemical reaction or covalent bonding.

For any medicament to be delivered, similar numbers may be generated whereby the carrier system will be balanced against the medicament.

It will be appreciated that the modifications and calculations in the tables follow the same general principles as described previously for balancing dipole moments using the sum of mole-moments. In this case, it is the sum of the molevan der Waals forces which is calculated and which appears to provide an effective correlation and predictor of success in formulating stable compositions with high solute/solvent ratios.

It should also be appreciated that the use of computer software, for chemical structure modelling, such as the Chem3D software, while speeding up the ability to fine tune the transdermal delivery system, is not essential since solubility and other data can generally be obtained from the literature or by direct experimentation, using the general guidelines and concepts discussed previously.

As in the case for balancing of dipole moments, in the present invention, the formulation of the solvent carrier system, which may be the above described SDS or any other appropriate non-aqueous or aqueous solvent-carrier system for the particular active agent or active agents and the particular disease or other condition to be treated, may be balanced for mole-van der Waals forces, when the active agent or agents are added thereto, as a predictor of solubility of the desired amount(s) of active agent(s) by bringing the sum of the mole-van der Waals forces for the solvent carrier system with active agent(s) to within ±20%, preferably within ±15%, especially preferably within ±10%, and most especially preferably within ±5%, of the sum of the mole-van der Waals forces of the solvent carrier system without the active agent(s).

When the difference between the sum of the mole-van der Waals forces of the solvent carrier system plus active agent is greater than about 20%, especially greater than about 15%, of the sum of mole-van der Waals forces for the solvent carrier system without active agent the desired amount of active agent will tend to be insoluble in the solvent carrier system or may precipitate from solution upon standing overnight. In the case of compositions containing two or more active agents, if the mole-van der Waals forces are not closely balanced, as described above, one or more of the active agents will tend to be insoluble in the solvent carrier system or otherwise precipitate out of solution.

TABLE 1

Diosgenin Base Solution

| Compound | Mole Wt. | Amt. (grams) | Amt./100 cc | Moles | Moles VW Forces | VW Forces |
|---|---|---|---|---|---|---|
| Diosgenin | 414.6 | | 0.25[1] | 0.0006 | 26.88 | 0.016 |
| Ethanol | 46.07 | 1068.75 | 54.38 | 1.18 | 2.01 | 2.375 |
| Water | 18 | 56.25 | 2.86 | 0.16 | 0 | 0 |
| Propylene Glycol | 76.01 | 828 | 42.13 | 0.55 | 4.10 | 2.272 |
| limonene | 136.24 | 2 | 0.10 | 0.0007 | 6.22 | 0.0046 |
| Vitamin E | 430.17 | 1 | 0.50 | 0.00012 | 20.60 | 0.0024 |
| D-Panthenol | 205.25 | 1.05 | 0.05 | 0.00026 | 10.82 | 0.0028 |
| Methylsulfonyl-methane (MSM) | 94.13 | 2 | 0.10 | 0.0011 | −0.34 | −0.0004 |
| Lauriciden | 181.97 | 5 | 0.25 | 0.0014 | 14.04 | 0.020 |
| Oxindole | 295 | 0.06 | 0.003 | 1.0E-05 | 13.66 | 0.0001 |
| Thiopropionic acid | 178.21 | 1 | 0.05 | 0.0003 | 6.61 | 0.001 |
| Forskolin | 410 | 0.2 | 0.01 | 2.5E-05 | 25.05 | 0.0006 |
| Totals | | 1965.31 | 100 | | | | stock solution + diosgenin = 4.694
stock solution w/out diosgenin = 4.678
difference = 0.016
percent difference = 0.34%
[1]Solubility limit determined experimentally

TABLE 2

Diosgenin System One

| Compound | Mole Wt. | Amt/100 cc | Moles | VW Forces | Mole VW Forces One |
|---|---|---|---|---|---|
| Diosgenin | 414.6 | 1.2[1] | 0.003 | 26.88 | 0.078 |
| Ethanol | 46.07 | 77.73 | 1.69 | 2.01 | 3.395 |
| Isopropyl Alcohol | 60.1 | 8.18 | 0.14 | 1.94 | 0.264 |
| Water | 18 | 2.30 | 0.13 | 0 | 0 |
| Propylene Glycol | 76.01 | 10.04 | 0.13 | 4.10 | 0.541 |
| limonene | 136.24 | 0 | 0 | | 0 |
| Vitamin E | 430.17 | 0 | 0 | | 0 |
| D-Panthenol | 205.25 | 0 | 0 | | 0 |
| MSM | 94.13 | 0 | 0 | | 0 |
| Lauriciden | 181.97 | 0.3 | 0.00 | 14.04 | 0.023 |
| Oxindole | 295 | 0.06 | 0.0002 | 13.66 | 0.003 |
| Thiopropionic acid | 178.21 | 0 | 0 | 6.61 | 0 |
| Forskolin | 410 | 0.2 | 0.0005 | 25.05 | 0.012 |
| Totals | | 100 | | | |

Diosgenin SysOne Mole VWF 4.316
STOCK SOL. 4.238
Diosgenin SysOne minus Stock Sol. 0.07
Percent Difference 1.84
[1]Stable solution; effective for transdermal delivery

TABLE 3

Diosgenin System Two

| Compound | Mole Wt. | Amt/100 cc | Moles | Mole VW Forces | VW Forces |
|---|---|---|---|---|---|
| Diosgenin | 414.6 | 1.5[1] | 0.0036 | 26.88 | 0.097 |
| Ethanol | 46.07 | 77.49 | 1.682 | 2.01 | 3.385 |
| Isopropyl Alcohol | 60.1 | 8.16 | 0.136 | 1.94 | 0.264 |
| Water | 18 | 2.29 | 0.127 | 0 | 0 |
| Propylene Glycol | 76.01 | 10.00 | 0.132 | 4.10 | 0.539 |
| limonene | 136.24 | 0 | 0 | | 0 |

TABLE 3-continued

Diosgenin System Two

| Compound | Mole Wt. | Amt/100 cc | Moles | Mole VW Forces | VW Forces |
|---|---|---|---|---|---|
| Vitamin E | 430.17 | 0 | 0 | | 0 |
| D-Panthenol | 205.25 | 0 | 0 | | 0 |
| MSM | 94.13 | 0 | 0 | | 0 |
| Lauriciden | 181.97 | 0.3 | 0.0016 | 14.05 | 0.023 |
| Oxindole | 295 | 0.06 | 0.0002 | 13.66 | 0.003 |
| Thiopropionic acid | 178.21 | 0 | 0 | 6.61 | 0 |
| Forskolin | 410 | 0.2 | 0.0005 | 25.05 | 0.012 |
| Totals | | 100 | | | |

Diosgenin Sol Mole VWF Two 4.323
STOCK SOL. 4.226
Diosgenin Sys Two minus Stock Sol. 0.097
Percent Difference 2.30
[1]Solution not stable; precipate forms upon standing overnight.

The following Table 4 illustrates how the balancing of molar van der Waals forces can be utilized as a predictor of the solubilization of amitriptyline in the stock delivery system. In this case the calculations for balancing molar van der Waals forces were made first using the Chem3D software and the solutions were thereafter formulated in the laboratory. The amount predicted to dissolve, 2.08 gm per 100 c.c., was within experimental error of the actual amount which would dissolve in the laboratory experiment. In this case, the system was balanced by increasing the amounts of methylsulfonylmethane and ethanol and decreasing the amount of propylene glycol.

TABLE 4

| | Mole Wt | SDS Amt/100 | SDS Moles | Mod. SDS Amt/100 | Moles | VW Forces | SDS + Drug VDW-Molar | SDS + Drug VDW-Molar |
|---|---|---|---|---|---|---|---|---|
| Amitriptyline | 277.41 | 2.00 | 0.007 | 2.08 | 0.0075 | 15.99 | 0.115 | 0.120 |
| MSM | 94.13 | | | 0.20 | 0.0021 | −0.39 | | −0.0008 |
| Ethanol | 46.07 | 54.38 | 1.18 | 61.99 | 1.35 | 2.01 | 2.375 | 2.708 |
| Water | 18 | 2.86 | 0.16 | 1.86 | 0.16 | 0 | 0 | 0 |
| Propylene glycol | 76.01 | 42.13 | 0.55 | 33.70 | 0.44 | 4.10 | 2.272 | 1.817 |
| limonene | 136.24 | 0.10 | 0.0007 | 0.10 | 0.0006 | 6.22 | 0.005 | 0.004 |
| Vitamin E | 430.17 | 0.05 | 0.0001 | 0.05 | 9E-05 | 20.60 | 0.002 | 0.002 |
| D-panthenol | 205.25 | 0.05 | 0.0003 | 0.05 | 0.0002 | 10.81 | 0.003 | 0.002 |
| MSM | 94.13 | 0.10 | 0.001 | 0.10 | 0.0009 | −0.39 | −0.0004 | −0.0003 |
| Lauriciden | 181.97 | 0.25 | 0.001 | 0.25 | 0.001 | 14.05 | 0.020 | 0.016 |
| Oxindole | 295 | 0.003 | 1E-05 | 0.003 | 8E-06 | 13.66 | 0.0001 | 0.0001 |
| Thioproprionic acid | 178.21 | 0.05 | 0.0003 | 0.05 | 0.0002 | 6.60 | 0.002 | 0.002 |
| Forskolin | 410 | 0.01 | 2.5E-05 | 0.01 | 2E-05 | 25.05 | 0.0006 | 0.0005 |
| | | | | 100 | | | | |

SDS + Drug = 4.794 4.670
SDS = 4.679

The following Table 5 illustrates the calculation of the mole-moment for a typical Stock Delivery System (SDS) according to the invention:

TABLE 5

| Compound | Mole Wt | SDS Amt Used | Amt/100 | Moles | dipole Moment | Mole Moment |
|---|---|---|---|---|---|---|
| Ethanol | 46.07 | 1068.75 | 54.38 | 1.18 | 1.78 | 2.10 |
| Water | 18 | 56.25 | 2.86 | 0.16 | 1.85 | 0.29 |

TABLE 5-continued

| Compound | Mole Wt | SDS Amt Used | Amt/100 | Moles | dipole Moment | Mole Moment |
|---|---|---|---|---|---|---|
| Propylene Glycol | 76.01 | 828 | 42.13 | 0.55 | 1.45 | 0.80 |
| limonene | 136.24 | 2 | 0.10 | 0.0007 | 0.365 | 0.0003 |
| Vitamin E | 430.17 | 1 | 0.05 | 0.0001 | 0.835 | 9.9E-05 |
| D-panthenol | 205.25 | 1.05 | 0.05 | 0.00026 | 4.33 | 0.001 |
| MSM | 94.13 | 2 | 0.10 | 0.0011 | 4.51 | 0.005 |
| Lauriciden | 181.97 | 5 | 0.25 | 0.0014 | 3.08 | 0.004 |
| Oxindole | 295 | 0.06 | 0.003 | 1.03E-05 | 1.42 | 1.5E-05 |
| Thiopropionic Acid | 178.21 | 1 | 0.05 | 0.00029 | 3.94 | 0.001 |
| Forskolin | 410 | 0.2 | 0.01 | 2.5E-05 | 4.48 | 0.0001 |
|  |  | 1965.31 | 100 |  |  |  |
| SUM Mole Moments |  |  |  |  |  | 3.20 |

Table 6 shows van der Waals force values for various hormonal active agents:

TABLE 6

| Hormone | VW Forces |
|---|---|
| Testosterone | 16.17 |
| Estrone | 13.74 |
| Estradiol | 14.87 |
| Estriol | 13.89 |
| DHEA | 16.48 |
| 17 OH Pregnenolone | 18.16 |
| Pregnenolone | 16.78 |
| Progesterone | 15.93 |
| Diosgenin | 26.88 |

Use of the invention methodology for forming a topical composition for transdermal delivery of hydroxyzine at a predetermined or target dosage of about 45 to 50 mg per cubic centimeter is illustrated in the following Table 7:

TABLE 7

| Compound | Mole Wt | SDS[1] Amt/100 | H-1[2] Amt/100 | H-2[3] Amt/100 | Sol Moles | Two Moles | dipole Moment | Mole Moment | VW Forces |
|---|---|---|---|---|---|---|---|---|---|
| Hydroxyzine | 374.91 | 5.0 | 5.0 | 4.55 | 0.013 | 0.012 | 0.57 | 0.0076 | 22.72 |
| HSM | 94.13 | | 2.0 | 1.0 | 0.021 | | 4.51 | 0.096 | −0.39 |
| Ethanol | 46.07 | 54.38 | 54.38 | 58.07 | 1.18 | 1.26 | 1.78 | 2.10 | 2.01 |
| Water | 18 | 2.86 | 2.86 | | 0.16 | | 1.85 | 0.29 | 0 |
| Propylene Glycol | 76.01 | 42.13 | 42.13 | 38.30 | 0.55 | 0.50 | 1.45 | 0.804 | 4.10 |
| limonene | 136.24 | 0.10 | 0.001 | 0.10 | 0.0007 | | 0.36 | 0.0002 | 6.23 |
| Vit E | 430.17 | 0.05 | 0.051 | | 0.0001 | | 0.83 | 0.0001 | 20.00 |
| D-panthenol | 205.25 | 0.05 | 0.053 | | 0.003 | | 4.33 | 0.001 | 10.82 |
| HSM | 94.13 | 0.10 | 0.10 | | 0.001 | | 4.51 | 0.005 | −0.39 |
| Lauriciden | 181.97 | 0.25 | 0.25 | | 0.001 | | 3.08 | 0.004 | 14.05 |
| Oxindole | 295 | 0.003 | 0.003 | | 1E-05 | | 1.42 | 1.5E-05 | 13.66 |
| Thiopropionic acid | 178.21 | 0.05 | 0.05 | | 0.0002 | | 3.94 | 0.001 | 6.61 |
| Forskolin | 410 | 0.20 | 0.20 | | 0.005 | | 4.48 | 0.002 | 25.05 |

[1] Initial Attempt added Hydroxyzine to Stock Sol.
[2] First modification added additional MSM
[3] Second modification increased Ethanol and reduced additional MSM

TABLE 7

| H-0 Mole-VDW | H-1 Mole-VDW | H-2 Mole-VDW |
|---|---|---|
| 0.303 | 0.303 | 0.276 |
| | −0.0080 | −0.0083 |
| 2.375 | 2.375 | 2.536 |
| 0 | 0 | 0 |
| 2.272 | 2.272 | 2.065 |

TABLE 7-continued

| H-0 Mole-VDW | H-1 Mole-VDW | H-2 Mole-VDW |
|---|---|---|
| 0.0046 | 0.0046 | 0.0042 |
| 0.0024 | 0.0024 | 0.0022 |
| 0.0028 | 0.0028 | 0.0026 |
| −0.0004 | −0.0004 | −0.0004 |
| 0.0196 | 0.0196 | 0.017 |
| 0.00014 | 0.00014 | 0.0001 |
| .0019 | 0.0019 | 0.0017 |
| 0.0006 | 0.0006 | 0.0006 |
| 4.982 | 4.973 | 4.898 |

Although not wishing to be bound by any particular theory of operation, it is believed that the most adequate theory describing how the medicament finds its way, once inside the body, to the intended target site, is the so-called “information theory.” This theory asserts that medicaments are biologically active compounds for which the body develops particular affinities when challenge is present due to degenerative disease, infection or trauma. The affected tissues selectively attract and bind these substances as they encounter them in humor or tissue mediums while normal tissues seek to deflect the compounds away. Once the carrier medicament-complex arrives in the vicinity of the diseased or “abnormal” tissue, the attraction of the tissue receptors overcomes the weak association between the carrier and the medicament and the medicament is released intact and taken by the needy tissue. By a similar mechanism modifying agent components may be stripped from the complex prior to arriving at the needy tissue.

Examples of medicaments which may be incorporated in the transdermal delivery system of this invention are not particularly limited. Generally, any medications previously used or suggested as useful for delivery by any means, including transdermally, whether by patch or ointment or other topical formulation, may be used in this invention. Some areas where it is envisioned that the subject TDS will have particular benefits include pain relief (for safer dose of a prescription or non-prescription analgesic locally to the site of pain); antibiotic delivery, e.g., Ciprofloxacin (permitting higher dosages at the locus of the infection to above safe systemic levels); corticosteroids (for treating inflammatory indications with delivery bypassing the liver and minimizing systemic side effects); hormone replacement therapy (e.g., to deliver tri-estrogens to the non-carcinogenic androgen pathway along with the inclusion of mechanisms to offset the negative cosmetic side effects of this pathway); isoflavinoid cancer therapies (allowing high concentrations); hypertoxic chemotherapies (to raise local concentrations with reduced impact systemically).

More generally, any of the drugs listed in, for example, The Merck Index, or other pharmacopeia, may be used. For example, mention may be made of hormones, such as, DHEA sulphate, 17-hydroxy pregnenolone, testosterone, tri-estrogen; topical anesthetics, such as, lidocaine, procaine, dimethocaine, salicylic alcoholic; analgesics, such as, for example, mophine, Demerol®, Fentanyl®, sufentanil, acetaminophen, acetylsalicylic acid, bucetin, difenamizole, enfanamic acid, etodolac, fenoprofen, Ibuprofen, naproxen, suprofen; steroids, such as, for example, pregnenolone, pregnenolone acetate, progesterone; ACE-inhibitors; α-adrenergic agonists; β-adrenergic agonists; α-adrenergic blockers; β-adrenergic blockers; adrenocortical steroids; adrenocorticotropic hormones; alcohol deterrents; anabolic steroids; androgens, such as testosterones; anorexics; antacids; anthelmidines; antiacne and keratolytics; antiallergic, decongestants, antihistamines, glucocorticoids; antialopecia agents; antiandrogens; antianginals; antiarrhythmics; antiarthritic/antirheumatic; antiasthmatic; antibacterial (antibiotics), e.g., Ciprofloxacine, antifungal and antiviral agents; antineoplastics; anticholinergics; anticoagulants; anticonvulsants; antidepressants, e.g., 5-hydroxytryptophan; antidiabetics; antidiarrheal agents; antidiuretics; antidotes (e.g., acetaminophen poisoning, cyanide poisoning, heavy metal poisoning); antisyskinetics; anti-eczematic agents; antiemetics; antiestrogens; antihistamines; antihyperlipo-proteinemics; antihyperphosphatemics; antihypertensives, such as, e.g., clonidine, or other "beta-blockers"; antihyperthyroids; antihypotensives; antihypothyroids; anti-inflammatory (steroidal and non-steroidal, including, for example, the above-exemplified analgesics and other NSAIDs and steroidal inflammatories); antimalarial; antimigraines; antineoplastic agents; antiparkinsonian agents; antipruritics; antipsoriatics; antipsychotics; antipyretics; antiseptics and disinfectants; antispasmodics; antithrombotics; antitussives; antiulceratives; anxiolytics; astringents; benzodiazepine agonists; bronchodilators; calcium channel blockers; cardiotonics; chelating agents; choleretics; cholinergics; central nervous system (CNS) stimulants; digestive aids; diuretics; enzymes; estrogens; glucocorticoids; gonad-stimulating principles; gonadotropic hormones; other hormonal-type substances, such as, for example, melatonin, serotonin, liothyronine, histamine $H_2$-receptor antagonists; immunomodulators; immunosuppressants; lactation stimulating hormones; LH-RH agonists; lipotropics; monoamine oxidase inhibitors; muscle relaxants; narcotic antagonists; oxytocic agents; progestogens; prolactin inhibitors; prostaglandin/prostaglandin analogs; protease inhibitors; sedatives and hypnotic agents; vasodilators (cerebral, coronary and peripheral); vasoprotectants; vitamins.

In particular, the present invention may offer its most notable benefits in connection with active agents of high molecular weights for which prior known topical transdermal delivery systems were not effective or applicable. Thus, the compositions of this invention are highly useful and effective for active agents having molecular weights in excess of about 325 Daltons, especially higher than about 350 D, more especially higher than about 375 D and most especially higher than about 400 D, for example, 500 D and higher. Extremely high molecular weight substances such as calcitonin (MW=4500) human growth hormone (MW≈22,000) and other hormones, polypeptides and protein, may be solubilized in accordance with this invention by appropriate selection of solvents, e.g., fatty acid, and utilizing appropriate phospholipid chemistry for the oil phase and hydrophilic/lipophilic modulation by appropriate modifying agents. Moreover, the compositions of this invention may be formulated to delivery, per unit dosage, usually about 1 cc, at least about 0.25 mg, especially at least about 0.5 mg, especially, up to about 1 mg or higher of active ingredient, including such high molecular weight substances as described above.

Moreover, the effective dosage of the medicaments are generally substantially less than the effective dosage when administered orally or intravenously or intramuscularly; and a rule of thumb is that topical transdermal dosages are approximately one-seventh of the oral dosage. However, higher or lower dosages may be required or advantageous depending on the symptoms, whether intended for local or systemic administration, etc.

The invention will now be described with reference to the following non-limiting illustrative examples.

In the following examples the above described SDS was used, in the amounts indicated. Unless otherwise noted all of the ingredients are USP grade.

Example 1

The following composition (lotion) using the above described Stock Delivery System (SDS) is prepared with Diosgenin ((25R)-Spirost-5-en-3β-ol) as active ingredient; diosgenin is a large (MW=414.6), difficultly soluble soy isoflavone:

| Compound | Function | Amount (grams) |
| --- | --- | --- |
| Diosgenin | Active | 4.5 |
| 95% Ethanol/Sec-butanol | Primary Solvent | 410 c.c. |
| SDS | Primary Delivery | 90 c.c. |
| Alpha lipoic (Thioctic) Acid | Complexer | 0.5 |
| Methyl Sulfonyl Methane | Complex Former | 0.5 |
| 3,3'-Thiodipropionic Acid | Complexer | 0.2 |

A second lotion incorporating other soy isoflavanone compounds is prepared as follows:

| Compound | Function | Amount (grams) |
| --- | --- | --- |
| Genistein | Active | 5.0 |
| Daidzein | Active | 5.0 |
| Biochanin A | Active | 5.0 |
| Phosphatidyl Serine | Complexer | 25 c.c. |
| SDS | Primary Delivery | 500 c.c. |

In the above formula, daidzein is 4',7-dihydroxyisoflavone. Biochanin is the 4'-methyl ether of genistein (5,7-dihydroxy-3-(4-hydroxyphenyl)-4H-1-benzopyran-4-one; 4',5,7-trihydroxyisoflavone).

These two formulations when used in combination, are expected to be useful in the treatment of prostate cancer.

Example 2

A hormone replacement therapy formulation, especially useful in the treatment of Benign Prostatic Hyperplasia (BPH) using a lower concentration of soy isoflavanones, than in the formulations of Example 1, again in the form of a lotion, is prepared with the following ingredients:

| Compound | Function | Amount (grams) |
| --- | --- | --- |
| SDS | Primary Delivery | 500 c.c. |
| Diosgenin | Active | 2.5 |
| Dehydroepiandosterone | Skin Stabilizer/Active | 7.5 |
| Pregnenolone acetate | Skin Stabilizer/Active | 1.25 |
| Dopamine | Tonic | 0.1 |
| Para-aminobenzoic Acid | B Complex Former, Skin Stabilizer | 0.5 |
| 2-Diethylaminoethanol | Solute Modifier | 0.5 |
| Ascorbyl Palmitate | Solvent Modifier | 0.15 |

To enhance the cosmetic tonic properties of the above formulation, various cosmetic additives can be added to the above formula, for example, various plant extracts, such as, for example, extracts of camomile, rosemary, rose hip, horsetail, in amounts of, for example, 10 cc, 5 cc, 5 cc, and 5 cc, respectively.

Example 3

A similar, but milder, formulation to that of example 2, more suitable for a female cosmetic product is formulated as follows:

| Compound | Function | Amount (grams) |
| --- | --- | --- |
| SDS | Primary Delivery System | 300 |
| Pregnenolone acetate | Skin Stabilizer/Active | 1.0 |
| Diosgenin | Active | 0.6 |
| Dehydroepiandosterone | Skin Stabilizer/Active | 0.6 |
| Forskholi (extract, 40%) | | 65 mg. |
| 3-Hydroxy Tyramine (Dopamine) | Tonic | 50 mg. |
| Camomile Extract | Tonic | 5.0 cc |
| Ascorbyl Palmitate | Solvent Modifier | 0.3 |
| Para-aminobenzoic acid | B Complex Factor, Skin Stabilizer | 0.5 |
| 2-Diethylaminoethanol | Solute Modifier | 0.5 |
| Horsetail Extract | Tonic | 0.5 |
| 3,3'-Thiodiproprionic acid | Solute Modifier | 0.075 |
| Methyl Sulfonyl Methane | Solvent Modifier | 0.5 |

Example 4

The following female tonic preparation is prepared using the invention Stock Delivery System (SDS) to which pregnenolone acetate (PA) (3 mg/cc) is added:

| Compound | Function | Amount |
| --- | --- | --- |
| SDS + PA | Primary Delivery System | 100 cc + 0.3 g |
| Dehydroepiandosterone | Skin Stabilizer/Active | 1.25 g |
| Diosgenin | Active | 0.1 g |
| Hypericum | Tonic | 30.0 cc |
| Camomile Extract | Tonic | 10.0 cc |
| Rosemary Extract | Tonic | 10.0 cc |
| Rosehip Extract | Tonic | 10.0 cc |
| Horsetail Extract | Tonic | 10.0 cc |
| Pregnenolone acetate | Tonic | 100 mg |

Example 5

A tonic formulation, suitable for an over-the-counter hormonal product is produced with the following ingredients:

| Compound | Function | Amount (grams) |
| --- | --- | --- |
| SDS with Pregnenolone acetate (3 mg/cc) | Primary Delivery System Active | 100 cc 0.3 |
| Dehydroepiandosterone | Skin Stabilizer/Active | 1.25 |
| Diosgenin | Active | 0.1 |
| Hypericum | Tonic | 30 cc |
| Camomile Extract | Tonic | 10 cc |
| Rosemary Extract | Tonic | 10 cc |
| Rosehip Extract | Tonic | 10 cc |
| Horsetail Extract | Tonic | 10 cc |
| Pregnenolone acetate | Tonic | 100 mg |

Example 6

Another tonic formulation is prepared with the following ingredients:

| Compound | Function | Amount |
| --- | --- | --- |
| SDS | Primary Delivery System | 200 cc |
| Hypericum | Tonic | 20.0 cc |
| Glycyrrhiza | Tonic | 20.0 cc |
| NADH | Tonic | 6.0 mg |
| Dopamine | Tonic | 1.0 mg |
| Diosgenin | Active | 400 mg |
| Pregnenolone acetate | Tonic | 50 mg |
| Camomile Extract | Tonic | 5.0 cc |
| Rosemary Extract | Tonic | 1.0 cc |
| Rosehip Extract | Tonic | 1.0 cc |

Example 7

The following hormone therapy formulation, designed for female hormone replacement therapy, is prepared:

| Compound | Function | Amount |
| --- | --- | --- |
| SDS + Ferulic Acid + | Primary Delivery Complexer | 100 cc 2.0 g |
| Estriol | Active | 0.6 g |
| Dehydroepiandosterone | Skin Stabilizer/Active | 4.0 g |
| Progesterone | Tonic | 4.0 g |
| Pregnenolone Acetate | Tonic | 0.6 g |

-continued

| Compound | Function | Amount |
|---|---|---|
| Testosterone | Tonic | 5.0 g |
| Rx hormones, e.g., Triestrogens | Therapeutic element | perRx |

In the above formulation 0.5 grams of pregnenolone may be used in place of the 0.6 g of pregnenolone acetate.

Example 8

This example shows the preparation of an aqueous emulsion topical delivery system (OTC) according to the invention for the topical administration of the antibacterial Quaternium 28 (dimethyl benzethonium chloride):

| Compound | Function | Amount (wt. %) |
|---|---|---|
| Quaternium 28 | Active | 0.25 |
| Adogen ® DHT[1] | Solvent Modifier | 4.0 |
| Lauricidin ® | Skin desensitizer; anti-inflammatory | 6.0 |
| Methylsulfonyl-methane | Solvent Modifier | 2.4 |
| Ascorbyl Palmitate | Solute Modifier | 0.3 |
| Vitamin E Acetate | Solvent Modifier | 0.4 |
| Lemon Oil (Cold pressed, highest food grade) | Solvent Modifier | 0.8 |
| D-Panthenol | Solvent Modifier | 0.1 |
| Allantoin | Skin Stabilizer | 0.3 |
| Emu Oil | Natural Oil | 1.0 |
| Cetyl Palmitate | Skin Stabilizer | 0.25 |
| Varisoft ® 475 | Solvent Modifier | 4.0 |
| Decanoic Acid Triglyceride | Solvent Modifier | 0.3 |
| Water (DI) | Solvent | 79.9 |

The above ingredients are formulated into an emulsion in which the Varisoft, Adogen, Methylsulfonylmethane and Quaternium compounds are present in the aqueous phase; and Lauricidin, Ascorbyl palmitate, Cetyl palmitate, Vitamin E acetate, D-panthenol, allantoin, Emu Oil and decanoic acid triglyceride are present in the organic phase. The lemon oil is present at the interfaces of the oily and aqueous phases.
[1]dihydrogenated tallow dimethyl ammonium chloride; may also function as active ingredient, e.g., as a pain reliever, and also as an anti-irritant.

[1] dihydrogenated tallow dimethyl ammonium chloride; may also function as active ingredient, e.g., as a pain reliver, and also as an anti-irritant.

The above ingredients are formulated into an emulsion in which the Varisoft, Adogen, Methylsulfonylmethane and Quaternium compounds are present in the aqueous phase; and Lauricidin, Ascorbyl palmitate, Cetyl palmitate, Vitamin E acetate, D-panthenol, allantoin, Emu Oil and decanoic acid triglyceride are present in the organic phase. The lemon oil is present at the interfaces of the oily and aqueous phases.

The formulation may be prepared, for example, by combining the water soluble ingredients and heating to about 60° C. Separately, the organic phase ingredients are combined and heated to about 63° C. with care being taken to avoid temperatures above 70° C., preferably, not exceeding about 65° C. Thereafter, the above water soluble and oil soluble components are combined by adding the oil phase to the water phase and mixed in a closed, heated vessel. Water is added to achieve a workable consistency at which time mixing is continued with addition of the remaining water and after cooling to about 50° C. the lemon oil is added. Mixing is continued for about 1 hour at high, e.g., 1,200 rpm, speed, while continuing to cool. The vessel should, preferably, remain in the closed condition during this cooling. The cooling is conveniently accomplished using a cooling jacket on the outside of the mixing vessel. When the mixture cools to about 35° C. it is ready to be transferred to smaller containers for subsequent handling or transfer.

The mixture becomes quite viscous below about 50° C. so appropriate transfer procedures should be adopted.

For best results, during the mixing steps, the contents in the mixing vessel should be maintained at a level such that the depth of any vortex formed during mixing is about 25% of the depth in the vessel. As expected, the vortex depth will tend to increase as the temperature decreases and thickening increases. The mixing should be accomplished under conditions which avoid aeration.

Example 9

This example describes the results of an animal (mouse) study performed at St. Bartholomew's and The Royal London School of Medicine and Dentistry, Department of Experimental Pathology, to establish the efficacy of the topical delivery system, based on the Stock Delivery System of this invention for transdermal delivery of Cystamine (2,2'-dithiobisethanamine). A Murine Chronic Granulomatous Air-Pouch Model was used for evaluation of the delivery of the drug with SDS versus a control vehicle alone; control vehicle plus drug; and SDS alone.

The Air-Pouch Model was selected as an attractive method for studying inflammatory processes since rodent air pouch has been shown to develop into a structure resembling the synovium of diarthrodial joints and in view of ease of induction and possibilities of serial sampling of fluid and tissue. In addition, the air pouch has been developed further in mice for use in the examination of the angiogenic response. The murine chronic granulomatous air pouch is advantageous for study in view of the ease of therapeutic manipulation in this species used and, further, the development of the vasculature may be readily assessed by dye incorporation assays. The metabolic responses of the lining cells of the murine air pouch was assessed for comparison to the enzyme induction seen in rheumatoid synoviocytes, and the model subsequently used for assessing the potential of varying agents to modulate the angiogenic response.

In this study, 1 milligram (mg) of cystamine was added to 0.5 cc of Standard Stock Solution (SDS) as previously described, or to a control vehicle (aqueous isopropanol). In each case, the active ingredient (cystamine) was administered in an amount of 30 mg per kilogram of body weight.

Mice (TO or BALB/c, for hormone studies, 30±5 g) were lightly anaesthetized with halothane. Three milliliters of air were injected subcutaneously into the scruff of the neck using a 25 G needle. The shape of the air pouch was controlled by manipulation during inflation. One day later, 0.5 ml Freund's complete adjuvant supplemented with 0.1% croton oil was injected into the air pouch using a 21 G needle. Animals were killed at various time points for assessment of pouch vascularity, histology and cleared air pouch preparations.

Vascularity was assessed by a modified form (see Kimura et al, [need citation] 1986) of the Carmine Red Vascular Casting technique. Mice were anaesthetized using hypnorm/hypnovel and kept warm on a heated box at 40° C. for 10 minutes. One milliliter (1 ml) of 25% carmine red dye in 10% gelatin at 40° C. was injected into the tail vein of each mouse. Cadavers were chilled at 4° C. for 4 hours and the granulomas dissected free. Granulomas were weighted after drying in an oven for 2 days at 56° C. The dried granulomas were digested for 24 hours at 56° C. in 0.9 ml of digestive solution (12 units ml$^{-1}$ papain in 0.05 M phosphate buffer, pH 7.0, supplemented with 0.33 g/liter N-acetyl cysteine)

for cotton-wrapped cartilage granulomas and 9 ml for air pouch granulomas. A volume of 0.1 ml or 1 ml of 4M sodium hydroxide (for each type of granuloma, respectively) was mixed well with each digest. The digests were centrifuged at 2000 g for 10 minutes and filtered through a 0.22 µm nitrocellulose disposable filter. The dye content was measured spectrophotometrically at 490 nm against a standard curve of dye from 1–100 µg/ml. Digests were diluted as appropriate to bring them onto the standard curve and blanked against non-injected control granulomas treated in the same way.

Results are expressed, below, as µg carmine red dye per mg dry tissue mass. In some cases, exudate was recovered from the air pouches at termination, 5M sodium hydroxide added to give a final concentration of 0.5M sodium hydroxide and processed as above to determine carmine content.

| Delivery System | Dry Weight of Granuloma (mg) |
| --- | --- |
| Control vehicle (CV) | 0.114 ± 0.113 |
| CV + cystamine | 0.115 ± 0.008 |
| SDS | 0.1334 ± 0.009 |
| SDS + cystamine | 0.082 ± 0.006* |
| SDS/[SDS + cystamine] | |

*p = 0.0291
**p = 0.0003

From the above results, namely, a decrease in dry weight of the granuloma, it is apparent that the SDS is highly effective as a delivery vehicle which, in fact, converts the normally sub-effective dose (30 mg/kg) of cystamine to an effective dose.

Example 10

This example is for an aqueous based weight reducing formula in which caffeine and the conjugated isomer of lineolic acid (CLA) are used as the primary active agents. The formulation was prepared without use of modelling software.

| Ingredient | Function | Amount (parts by weight) |
| --- | --- | --- |
| Caffeine | Active | 0.05 |
| CLA | Active | 1.2 |
| Aescin | Solute Modifier | 0.1 |
| Pyridoxal-5-Phosphate (P-5-P) | Active/Vitamin | 0.001 |
| Liquorice (20% glycyrrhizic Acid) | Active/Hormone Modulator | 0.05 |
| Ephedrine | Solute Modifier Active/CNS Stimulant | 0.5 |
| Theophilline | Solute Modifier + Active/CNS Stimulant | 1.5 |
| Olive Oil | Solvent Modifier | 4.0 |
| Carnitine | Solute Modifier | 0.1 |
| MSM | Solvent Modifier | 2.0 |
| Ascorbic Palmitate | Solvent Modifier | 0.15 |
| Lemon Oil | Solvent Modifier | 0.8 |
| Alpha-lipoic acid | Solute Modifier | 0.2 |
| Lauricidin | Skin Stabilizer | 1.0 |
| Adogen DHT | Solvent Modifier | 4.65 |
| Allantoin | Skin Stabilizer | 0.3 |
| Vitamin E acetate | Skin Stabilizer | 0.25 |
| Dexpanthenol | Solvent Modifier | 2.0 |
| Water | Primary Solvent | |

The above formulation is designed for patients with severe chronic obesity with cardiac complications. Therefore, forskolin is not included in the formula in view of its cardiotonic effects which, although only short-lived, is considered to present an unnecessary risk. However, under appropriate circumstances forskolin or equivalent may be added to the formulation with expected improvement in speed of absorption and total uptake. In addition, by more closely balancing moles-van der Waals forces to within about 15% or less further improvements in the penetration and performance characteristics would be achieved.

Example 11

This example is for a pain treating composition, formulated as an ointment.

| Ingredient | Amount (parts by weight) |
| --- | --- |
| Merguard | 0.125 |
| Verisoft 475 | 3.6 |
| Adogen DHT | 3.2 |
| Lauricidin | 6.0 |
| MSM | 2.4 |
| Ascorbic Palmitate | 0.3 |
| Vitamin E Acetate | 0.4 |
| Lemon Oil | 0.8 |
| Dexpanthenol | 0.1 |
| Allantoin | 0.7 |
| Olive Oil | 1.0 |
| Cetyl Palmitate | 0.25 |
| Dimethyl Benzethonium Chloride | 0.25 |
| Decanoic Acid Triglyceride | 0.7 |
| Sorbitan Palmitate | 0.7 |
| Water | 5.225 |

The sum of the total system moles-van der Waals forces is 0.598 while for the total system less active agent (Varisoft 475) the sum of moles-van der Waals forces is 0.516.

Example 12

The following composition is an aqueous cream formulation designed for promoting cellulite removal.

| Ingredient | Amount (parts by weight) |
| --- | --- |
| CLA | 0.3 |
| Aescin | 0.1 |
| P-5-P | 0.001 |
| Liquorice (20%) | 0.05 |
| Ephedrine | 0.5 |
| Theophilline | 1.5 |
| Olive Oil | 2.0 |
| Carnitine | 0.3 |
| MSM | 2.0 |
| Ascorbic Palmitate | 0.015 |
| Lemon Oil | 0.8 |
| Alpha lipoic acid | 0.2 |
| Lauricidin | 2.0 |
| Adogen DHT | 4.65 |
| Allantoin | 0.3 |
| Vitamin E acetate | 0.25 |
| Dexpanthenol | 2.0 |
| Propylene Glycol | 2.0 |
| Water | |

The difference between the moles-van der Waals forces of the carrier/solvent system (0.506) and the total system (carrier/solvent plus active ingredient—therophilline) (0.552) is about 8.33%

Example 13

This example describes the results of an in vitro trial based on the stock delivery system of this invention, for transdermal delivery of morphine (as morphine sulfate), in a Franz Diffusion Cell model.

Evaluation of Morphine Formulation

This morphine formulation is designed as a therapeutical product for cancer pain relief.

Presently, transdermal formulations developed for the purpose of cancer pain relief have not yet been found to be successful for practical use. One reason, is that the level of morphine required to show an analgesic effect is very high, in the order of 70 mg/day (in the case of applying to a 100 cm$^2$ area, a transdermal absorption rate of 27 µg/hr/cm$^2$ is necessary). If an absorption enhancer strong enough to have such a high level of morphine absorbed transdermally is used, it is inevitable that serious skin irritation will result.

The evaluation of the subject formulation was performed in vitro with skin taken from a hairless rat. Since the barrier ability of the stratum corneum does not differ between in vitro and in vivo status, transdermal absorption may be correlated evaluated with the in vitro skin permeation test.

Experiment 2 kinds of SDS vehicles were used:

SDS-L for topical use—lotion (see Table 8);

SDS-S for systemic use—lotion (see Table 9).

The morphine sulfate was supplied by Sankyo Pharmaceuticals, Japan.

TABLE 8

| Compound | Mole Wt | Amt (g)/100 ml |
| --- | --- | --- |
| Morphine Sulfate | 668.77 | 0.25 |
| SDS-L | | |
| MSM | 94.13 | 2 |
| Ethanol | 46.07 | 56.881 |
| Water | 18 | 2.862 |
| Propylene Glycol | 76.01 | 42.131 |
| limonene | 136.24 | 0.102 |
| Vit E | 430.17 | 0.051 |
| Dexpanthenol | 205.25 | 0.053 |
| MSM | 94.13 | 0.102 |
| Lauriciden | 181.97 | 0.254 |
| Oxindole | 295 | 0.003 |
| Thioproprionic Acid | 178.21 | 0.051 |
| Forskolin | 410 | 0.010 |

TABLE 9

| Compound | Mole Wt | Amt (g)/100 ml |
| --- | --- | --- |
| Morphine Sulphate | 668.77 | 0.25 |
| SDS-S | | |
| Ethanol | 46.07 | 57.243 |
| Acetone | 58.08 | 5.0 |
| Propylene Glycol | 76.01 | 42.131 |
| limonene | 136.24 | 0.102 |
| Vit E | 430.17 | 0.051 |
| Dexpanthenol | 205.25 | 0.053 |
| MSM | 94.13 | 0.102 |
| Lauriciden | 181.97 | 0.254 |
| Oxindole | 295 | 0.003 |
| Thioproprionic acid | 178.21 | 0.051 |
| Forskolin | 410 | 0.010 |
| Balancing Compoents | | |
| ATP | 507.17 | 0.25 |
| Limonene | 136.24 | 1.0 |
| DMAE | 89.14 | 1.0 |
| Benzyl Alcohol | 108.44 | 0.5 |
| MSM | 94.13 | 3.0 |

The standard stock solution, SDS-L, is not optimized for system perfusion. However, for the systemic stock solution, SDS-S, the additional MSM, additional limonene, DMAE and benzyl alcohol are added to the solution to balance the formula as previously described. Thus, the sum of the products van der Waals-moles for the ingredients of SDS-S (namely, ethanol, acetone, propylene glycol, Vitamin E, dexpanthenol, methylsulfonylmethane (MSM), lauriciden, oxindole, thioproprionic acid, and Forskolin) is 4.742, whereas the sum of the products VDW-moles for the final formula (including morphine sulfate, additional MSM, additional limonene, dimethylaminoethanol (DMAE), and benzyl alcohol) is 4.861, a difference of only about 2.44%. additional limonene, dimethylaminoethanol (DMAE) and benzyl alcohol) is 4.861, a difference of only about 2.44%.

Skin Permeation Test

A vertical standing static type Franz Cell is employed. The receptor phase is maintained at 37° C. by circulating uniformly heated water.

Skin is taken from the abdomen of a hairless rat, male, 12 weeks of age, purchased from Charles River Laboratories, and the skin is stored for two weeks at −60°. Just before use the skin is gently thawed to room temperature and then cut into circular shapes with a diameter of 3.5 cm and set into the Franz Cell device.

The topical and systemic preparations are prepared by adding 28 mg of morphine sulfate to 10 ml each of SDS-L and SDS-S while stirring at room temperature until the morphine sulfate is completely dissolved and allowing the mixture to stand overnight, while tightly sealed.

In order to compare effectiveness of the formulations as a lotion and as a patch, the evaluations are made on two kinds of applications: open condition, which mimics the application of a lotion formulation and, closed condition, which mimics the application of a patch formulation, as follows:

(i) Open Condition

At the beginning of the skin permeation test, 1 ml of the morphine sulfate combined with SDS-L or morphine sulfate combined with SDS-S is placed in the Donor chamber of the Franz Cell. Air is introduced for 10 minutes by a drier to volatilize the volatile components in the vehicle. The Donor chamber is kept open until the completion of the test.

(ii) Closed Condition

At the beginning of the skin permeation test, 1 ml each of the morphine sulfate combined with SDS-L or morphine sulfate combined with SDS-S is placed in the Donor chamber of the Franz Cell. The Donor chamber is kept completely sealed until the completion of the test.

Isotonic phosphate buffer, pH 7.2, consisting of 0.033 mM sodium phosphate, 7.4% NaCl and 1% NaN$_3$ (preservative) is used as the receptor solution.

At each sampling time, established beforehand, 1.8 ml of the solution in the receptor chamber is sampled, and the same volume of receptor solution is added to the receptor chamber.

The concentration of morphine sulfate in each receptor solution sampled is determined quantitatively by HPLC.

Based on the morphine sulfate concentration in the receptor solution obtained as above, the amount of morphine sulfate permeated per 1 cm$^2$ of skin is cumulatively calculated, then plotted against each sampling time. On the resulting skin permeation profiles, the region where there is a linear relation between the permeated morphine sulfate concentrations and the sampling times is chosen. Then the linear equation that best fit the region is determined by the least squares method. The "permeation flux" is obtained from the slope and the "lag time" from the time-axis intercept. The tests are repeated three times and the average and standard deviation (SD) of the "permeation flux" and the "lag time" are calculated.

Results 1. pH Values of Morphine Sulfate Combined with SDS-L and Morphine Sulfate Combined with SDS-S The pH values of vehicle combined with morphine sulfate (at 2.6 mg morphine sulfate/ml) was 6.14 for SDS-L and 5.77 for SDS-S, respectively. Both formulations are non-toxic to the skin.

2. Volatility of Solvent under Ooen Conditions

Approximately half the volume of the solvent remained (not volatized) after ventilation for 10 minutes with the drier. After extending the test for 29 hours, about 1/10 volume of the solvent still remained in the donor cell.

3. Skin permeation of the Morphine Sulfate from the Stock Solution

Figure 2:
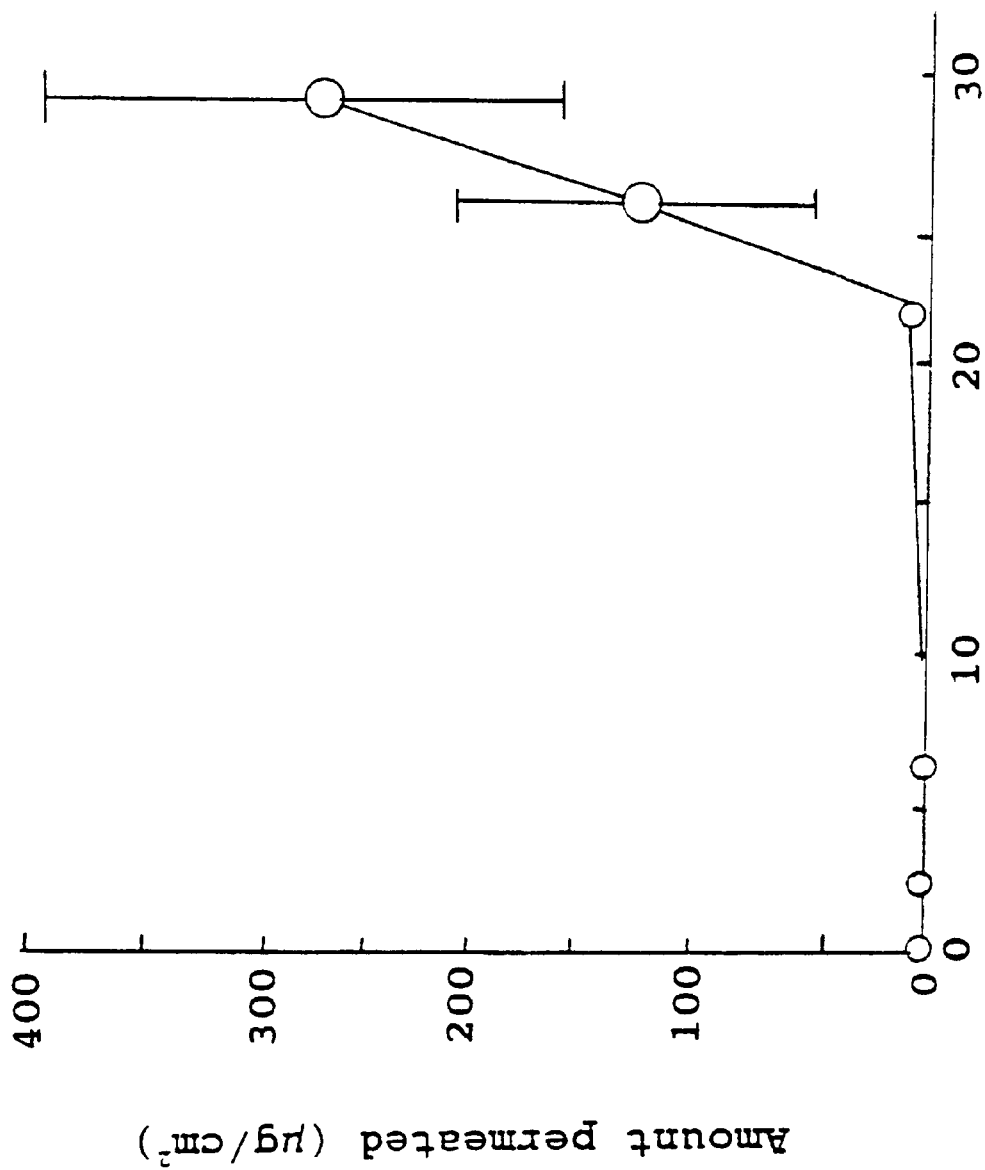
FIG. 2 is a graphical representation similar to FIG. 1 but for testing under closed (patch) conditions using the SDS-L delivery system described in Example 13.
Figure 3:
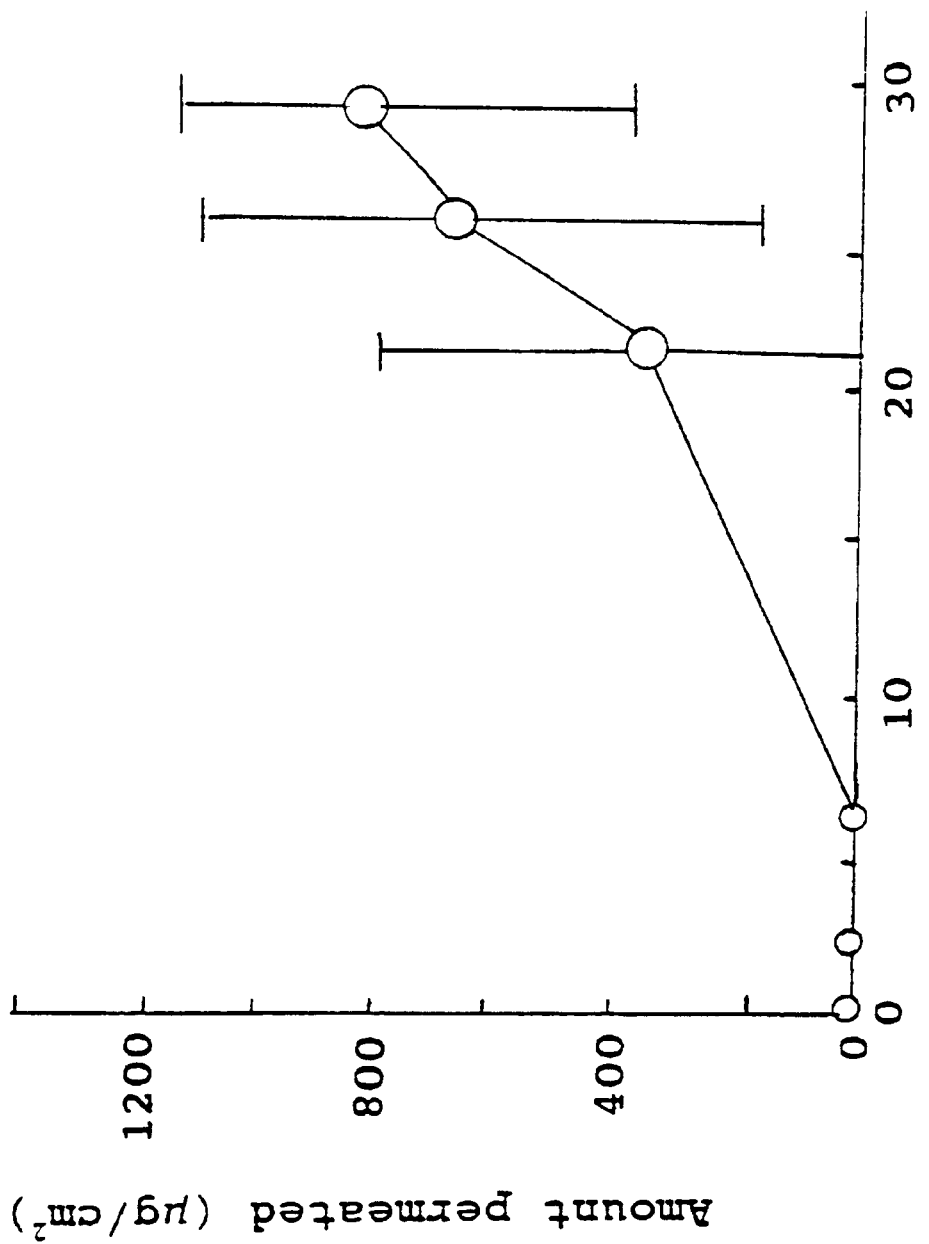
FIG. 3 is a graphical representation similar to FIG. 1 but using the topical delivery system SDS-S, as described in Example 13.
Figure 4:
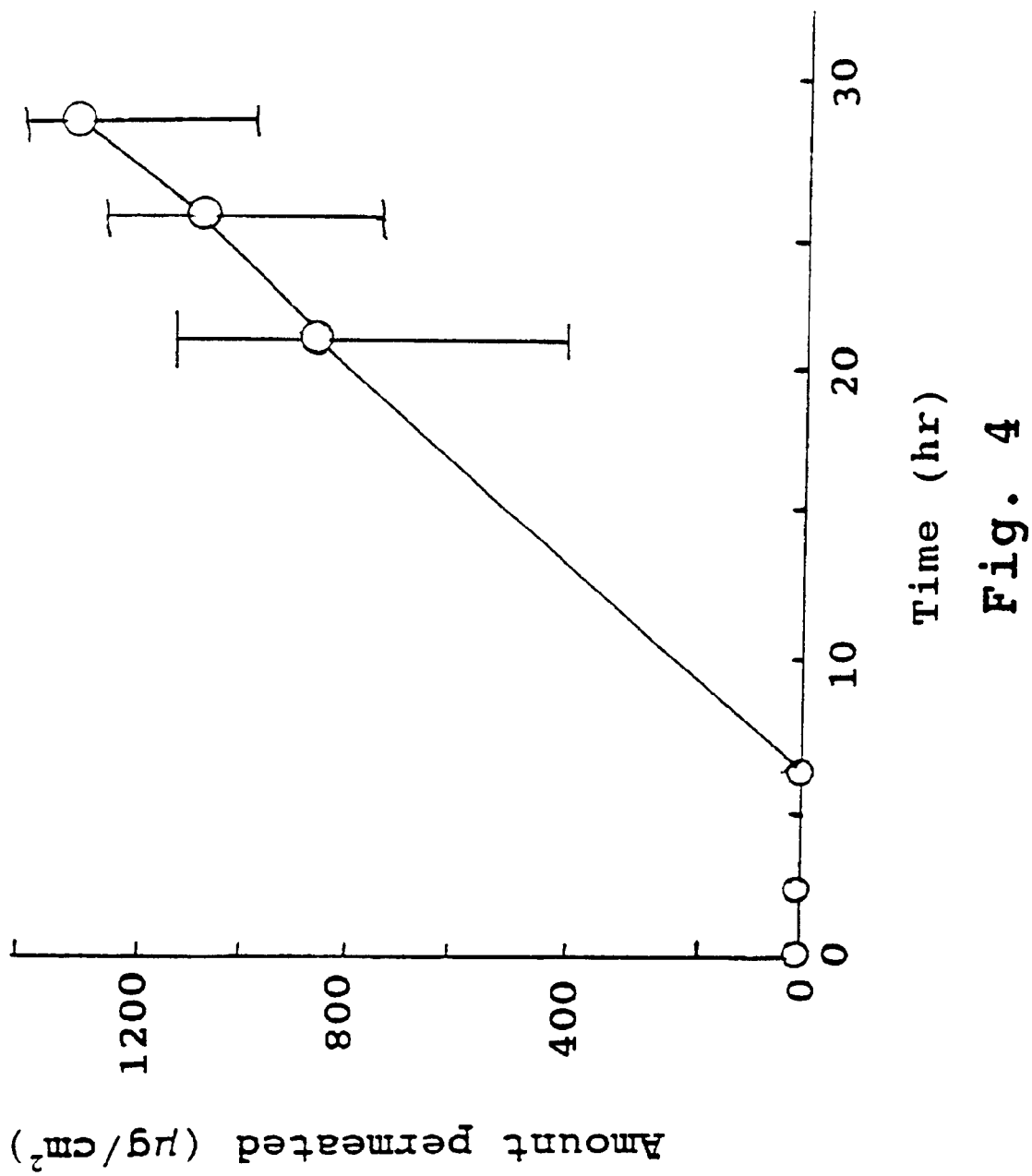
FIG. 4 is a graphical representation similar to FIG. 2 (closed patch application) for transdermal delivery of morphine, but using the topical delivery system SDS-S.

Tables 10 and 13 and FIGS. 1–4 show the cumulative permeated amount of morphine sulfate per 1 cm² of hairless rat skin over time. Table 14 shows the permeation of flux and lag time of morphine sulfate obtained from the permeation profiles in FIG. 1. For both SDS-L and SDS-S morphine sulfate is detected in the receptor solution after 6 hours. Thereafter, the permeation flux is approximately twice as fast in SDS-S than in SDS-L. In the case of SDS-L, there is little or no difference in the permeation flux or the lag time between the open conditions and the closed conditions. In the case of SDS-S, there is also little or no difference in the flux or lag time between open and closed conditions.

TABLE 10

Amount of morphine sulfate through 1 cm² of hairless rat skin from SDS-L (open condition)

| Time (hr) | Amount of morphine sulfate through 1 cm² of hairless rat skin (ug/cm²) | | | | |
|---|---|---|---|---|---|
| | s-1 | s-2 | s-3 | mean | sd[1] |
| 0 | 0 | 0 | 0 | 0 | 0 |
| 3 | 0 | 0 | 0 | 0 | 0 |
| 6 | 0 | 0 | 0 | 0 | 0 |
| 22 | 118 | 6 | 8 | 44 | 64 |
| 26 | 373 | 44 | 48 | 155 | 189 |
| 29 | 564 | 141 | 119 | 275 | 251 |

[1]standard deviation

TABLE 11

Amount of morphine sulfate through 1 cm² of hairless rat skin from SDS-L (closed condition)

| Time (hr) | Amount of morphine sulfate through 1 cm² of hairless rat skin (ug/cm²) | | | | |
|---|---|---|---|---|---|
| | s-1 | s-2 | s-3 | mean | sd[1] |
| 0 | 0 | 0 | 0 | 0 | 0 |
| 3 | 0 | 0 | 0 | 0 | 0 |
| 6 | 0 | 0 | 0 | 0 | 0 |
| 22 | 6 | 22 | 7 | 12 | 9 |
| 26 | 40 | 179 | 158 | 126 | 75 |
| 29 | 158 | 327 | 324 | 270 | 97 |

[1]standard deviation

TABLE 12

Amount of morphine sulfate through 1 cm² of hairless rat skin from SDS-S (open condition)

| Time (hr) | Amount of morphine sulfate through 1 cm² of hairless rat skin (ug/cm²) | | | | |
|---|---|---|---|---|---|
| | s-1 | s-2 | s-3 | mean | sd[1] |
| 0 | 0 | 0 | 0 | 0 | 0 |
| 3 | 0 | 0 | 0 | 0 | 0 |

TABLE 12-continued

Amount of morphine sulfate through 1 cm² of hairless rat skin from SDS-S (open condition)

| Time (hr) | Amount of morphine sulfate through 1 cm² of hairless rat skin (ug/cm²) | | | | |
|---|---|---|---|---|---|
| | s-1 | s-2 | s-3 | mean | sd[1] |
| 6 | 0 | 0 | 0 | 0 | 0 |
| 22 | 67 | 865 | 125 | 352 | 445 |
| 26 | 290 | 1140 | 447 | 626 | 452 |
| 29 | 464 | 1263 | 694 | 807 | 412 |

[1]standard deviation

TABLE 13

Amount of morphine sulfate through 1 cm² of hairless rat skin from SDS-S (closed condition)

| Time (hr) | Amount of morphine sulfate through 1 cm² of hairless rat skin (ug/cm²) | | | | |
|---|---|---|---|---|---|
| | s-1 | s-2 | s-3 | mean | sd[1] |
| 0 | 0 | 0 | 0 | 0 | 0 |
| 3 | 0 | 0 | 0 | 0 | 0 |
| 6 | 0 | 0 | 0 | 0 | 0 |
| 22 | 717 | 599 | 1091 | 802 | 257 |
| 26 | 1040 | 940 | 1256 | 1079 | 162 |
| 29 | 1256 | 1112 | 1375 | 1248 | 132 |

[1]standard deviation

TABLE 14

Permeation flux and lag time of morphine sulphate from SDS-L or SDS-S through hairless rat skin

| formulation | application method | flux ($\mu$g/hr/cm²) | lag time (hr) |
|---|---|---|---|
| MS-1 | open | 33± | 21 ± 1 |
| | closed | 36± | 22 ± 0 |
| MS-2 | open | 65± | 16 ± 8 |
| | closed | 64± | 7 ± 10 |

Example 14

This example describes the result of an animal (hairless rat) study performed to further establish the efficacy of the topical delivery system, based on the stock delivery system of this invention for transdermal delivery of morphine (mol. Wt. 285.34) and also for acylovir (mol. Wt. 225.21) and testosterone (mol. Wt. 288.43). The acyclovir and testosterone formulations are shown in Tables 15 and 16, respectively. The morphine formulation is shown in Table 9 above. A pilot trial is performed on three hairless rats, during which a baseline blood sample is drawn, then 1 ml of the topical delivery system containing a titrated dose of each of the three test drugs is administered to each of the rats. Samples are harvested at 30 and 60 minutes. The results are as follows:

| Medicament | Dose in 1 ml | Baseline | 30 minutes | 60 minutes |
|---|---|---|---|---|
| Morphine | 2.5 mg | 0 | Ins. Sample | 45 nmol/L |
| Testosterone | 5 mg | 165 | 1,552 ng/dl | 1600 ng/dl |
| Acyclovir | | 0 | | |

In view of these encouraging results a full-scale protocol trial is performed on 15 hairless rats, divided into three groups of five rats each. One group is dosed with the morphine formulation of Table 10, one with the testosterone formulation of Table 11 and one with the acylovir formulation of Table 12. Samples for the morphine and acyclovir groups are taken at 30 minutes, 60 minutes and 120 minutes. Samples from the testosterone group are taken at Baseline—0 minutes, 30 minutes and 60 minutes. The results are as follows:

| Medicament | Dose in 1 ml | Baseline | 30 minutes | 60 minutes |
|---|---|---|---|---|
| Morphine | 2.5 mg | 0 | nmol/L | nmol/L |
| Acyclovir | | 0 | ng/dl | ng/dl |
| Testosterone | 5 mg | 165 | ng/dl | ng/dl |

Testosterone levels are increased 10-fold in one hour. A 2.5 mg dose of morphine, a dose which would be considered insufficient to accomplish a therapeutic outcome if dosed intravenously, provides blood levels equivalent to a 10 mg IV dose. Further, morphine is considered extremely difficult to deliver transdermally due to its highly lipophilic character.

The kinetic outcomes for all three molecules would be sufficient to accomplish therapeutic doses in human beings.

TABLE 15

| Acyclovir Formulation | | |
|---|---|---|
| Compound | Mole Wt. | Amt/100 ml |
| Acyclovir | 225.09 | |
| MSM | 94.13 | 3 |
| SDS | | |
| VitE | 430.17 | 0.051 |
| Dexpanthenol | 205.25 | 0.053 |
| MSM | 94.13 | 0.10 |
| Lauriciden | 181.97 | 0.25 |
| Oxindole | 295 | 0.003 |
| Forskolin | 410 | 0.010 |

The sum of moles-van der Waals forces for the SDS components is 0.0252 while the sum of moles-van der Waals forces for the SDS plus acyclovir and additional MSM is 0.0353.

TABLE 16

| Testosterone Formulation | | |
|---|---|---|
| Compound | Mole Wt. | Amt/100 ml |
| Testosterone | 288.4 | 5.0 |
| Ethanol | 46.07 | 54.381 |
| Water | 18 | 2.862 |
| Propylene Glycol | 76.01 | 42.131 |
| limonene | 136.24 | 0.102 |
| VitE | 430.17 | 0.051 |

TABLE 16-continued

| Testosterone Formulation | | |
|---|---|---|
| Compound | Mole Wt. | Amt/100 ml |
| Dexpanthenol | 205.25 | 0.053 |
| MSM | 94.13 | 0.102 |
| Lauriciden | 181.97 | 0.254 |
| Oxindole alkaloid | 295 | 0.003 |
| Forskolin | 410 | 0.010 |

In order to determine the transdermal absorption of testosterone from this formulation, the formulation is applied to rat skin (n=6) and the amount absorbed through the skin is measured at 0, 30 and 60 minutes. The results obtained are shown in the following Table 17.

TABLE 17

| Testosterone absorption through the skin Plasma testosterone, ng/gl | | | | | | | | |
|---|---|---|---|---|---|---|---|---|
| Time | Rat 1 | Rat 2 | Rat 3 | Rat 4 | Rat 5 | Rat 6 | Mean | Median |
| 0 | 171 | 50 | 211 | 229 | 366 | 165 | 199 | 191 |
| 30 | 815 | 152 | 668 | 893 | 1577 | 1552 | 943 | 854 |
| 60 | 542 | 222 | 553 | 1321 | 2137 | >1600 | 1062 | 937 |

Example 15

The following lotion for transdermal delivery of male hormones is prepared.

| Compound | Mole Wt. | Amt/100 ml |
|---|---|---|
| DHEA | 288.4 | 1231 |
| Diosgenin | 414.6 | 0.115 |
| Androstenedione | 286.4 | 3.007 |
| Ethanol | 46.07 | 70.0 |
| Acetone | 58.08 | |
| water | 18 | 2.95 |
| Propylene Glycol | 76.01 | 22.0 |
| limonene | 136.24 | 0.10 |
| VitE | 430.17 | 0.06 |
| Dexpanthenol | 205.25 | 0.06 |
| MSM | 94.13 | 2.0 |
| Lauriciden | 181.97 | 0.20 |
| Oxindole | 295 | 0.01 |
| Thioproprionic acid | 178.21 | |
| Forskolin | 410 | 0.04 |
| Indole 3-Carbinol | | |
| Rosemary | | |

Example 16

This example is directed to a formulation for transdermal delivery of human growth hormone (HGH) (MW≈20,000) using a modified form of the standard stock delivery system according to this invention:

| | Amt/100 ml |
|---|---|
| HGH | 0.20 |
| Cyclodextrin | 5.0 |
| MSM | 1.5 |
| Vitamin E | 0.1 |
| Dexpanthenol | 0.055 |

-continued

| Ingredient | Amt/100 ml |
|---|---|
| Phytantriol | 0.025 |
| Oxindole | 0.15 |
| Forskolin | 0.50 |
| Tween 80 | 0.924 |
| Ceterath 20 | 1.5 |
| Guaifenenesin | 0.6 |
| Inositol | 0.6 |
| Propylene Glycol | 100.0 |
| Water | 10.0 |

Example 17

This example illustrates modification of the proportions of the active ingredients and delivery system to match the physiochemical properties (here, van der Waals forces) of the active ingredients and carrier system, to maximize effectiveness of the transdermal delivery of the active ingredients. In this case, the active ingredients, including the combination of Lorazepam and Ibuprofen, provide an anxiolytic or muscle relaxant treatment.

| Ingredient | Formula 17-A Amt/100 ml | Formula 17-B Amt/100 ml |
|---|---|---|
| Flubiprofen | 1.0 | 0.75 |
| Diazepam | 0.5 | 0.5 |
| Ibuprofen | 0.8 | 0.8 |
| Lorazepam | 0.3 | 0.3 |
| MSM | 4.0 | 4.0 |
| Ethanol | 56.9 | 56.9 |
| Water | 18.0 | 18.0 |
| Propylene Glycol | 42.1 | 42.1 |
| Limonene | 0.10 | 0.10 |
| Vitamin E | 0.05 | 0.05 |
| Dexpanthenol | 0.05 | 0.05 |
| MSM | 0.10 | 0.10 |
| Lauriciden | 0.25 | 0.25 |
| Oxindole | 0.003 | 0.003 |
| Thioproprionic Acid | 0.05 | 0.05 |
| Forskolin | 0.01 | 0.01 |
| Vinpocetine | 0.10 | 0.10 |
| Resveratrol | 0.02 | 0.02 |
| Emodin | 0.01 | 0.01 |
| Cyclobenzaprine HCl | 0.50 | 0.80 |
| Inositol | 0.60 | 0.60 |
| Guaifenenesin | 0.60 | 0.60 |
| Prozac | 1.0 | 0.5 |
| GABA | 1.0 | 1.0 |

For formula 17-A the sum of moles-van der Waals (VDW) for delivery system is 2.892 while for the delivery system and actives, the sum is 5.021. However, for formula 17-B the sume of moles-VDW is 2.838 for delivery system and 2.9687 for delivery system plus actives.

REFERENCES

1. T. K. Ghosh, et al., Methods of Enhancement of Transdermal Drug Delivery, Parts I, IIa & IIb, *Chemical Permeation Enhancers*, Pharm, Tech. 17(3): 72–98m 17(4):62–89m 17(5): 68–76 (1993).
2. Crouch, James E., *Functional Human Anatomy*, Lea & Fibiger, LOCCN 65-12968, Chapter 6, pp. 88–97, 1965.
3. K. Tojo, *Random Brick Model for Drug Transport Across Stratum Corneum*, J. Pharm. Sci., 76:889–891.
4. S. D. Roy, Preformulation Aspects of Transdermal Delivery Systems, In: *Transdermal and Topical Drug Delivery Systems*, Eds. T. K. Ghosh, W. R. Pfister, S. I. Yum, Interpharm Press, Inc., Buffalo Grove, Ill., 1997.
5. K. Gjesdal, et al., Transdermal Nitrate Therapy: Bioavailability During Exercise Increase Transiently after the Daily Change of the Patch, Brit. J. Clin. Pharmacol. 31:560–562 (1991).
6. K. Tojo, The Prediction of Transdermal Permeation: Mathematical Models, In: *Transdermal and Topical Drug Delivery Systems*, Eds., T. K. Ghosh, et al., Interpharm Press, Buffalo Grove, Ill., 1997.
7. I. Diez, et al., A Comparative In Vitro Study of Transdermal Absorption of a Series of Calcium Antagonist, J. Pharm. Sci. 80:931–934 (1991).
8. W. R. Pfister, et al., Permeation Enhancer Compatible with Transdermal Drug Delivery Systems, Parts I & II: Selection and Formulation Considerations, Pharm. Tech. 14(9):132–140, 14(10):56–60.
9. C. D. Vaughn, Using Solubility Parameters in Cosmetic Formulations, J. Soc. Cosmet. Chem. 36:319–333 (1985).
10. J. W. Streilein, In: *Immune Mechanisms in Cutaneous Diseases*, Ed. D. A. Norris, Marcel Dekker, Inc., New York, pp. 73–96 (1989).
11. J. Ademola, et al., Safety Assessment of Transdermal and Topical Dermatological Products In: *Transdermal and Topical Drug Delivery Systems*, Eds. T. K. Ghosh, et al., Interpharm Press, Inc., Buffalo Grove, Ill., (1997).
12. P. Liu, et al., Quantitative Evaluation of Ethanol Effects on Diffusion and Metabolism of β-Estradiol in Hairless Mouse Skin, Pharm. Res. 8:865–872 (1991).
13. Lubert Stryer, Biochemistry, 2nd Edition, Chapter 35, pp. 839–858, W. H. Freeman, Co., New York, (1981).
14. Kenneth B. Seamon, et al., Forskolin: Unique Diterpene Activator of Adenylate Cyclase in Membranes and Intact Cells; PNAS, vol. 78, no. 6, pp. 3363–3367 (June 1981).
15. Hermann P. T. Ammon, et al., Forskolin: From Ayurvedic Remedy to a Moder Agent; Planta Medica, pp. 473–476 (1985).

What is claimed is:

1. A liquid carrier composition effective for the transdermal delivery of a medicament having a given polarity, said formulation comprising
   (a) at least one non-aqueous non-toxic solvent selected from the group consisting of lower aliphatic mono- and poly-hydroxy compounds;
   (b) limonene, lemon oil or mixture of limonene and lemon oil;
   (c) methylsulfonylmethane;
   (d) a skin stabilizer which comprises at least one compound selected from the group consisting of an aliphatic carboxylic acid having from 8 to 32 carbon atoms, an ester of said aliphatic carboxylic acid with an aliphatic alcohol having from 1 to 20 carbon atoms, wherein said ester has a total of from 9 to 36 carbon atoms; and Vitamin D3;
   (e) a solute modifier which comprises a compound selected from the group consisting of 3,3'-thiodipropionic acid, an ester thereof, and a salt thereof; an oxindole alkaloid, a polyphenolic flavonoid, a sugar adduct of a gluconuide, isoflavones, phosphatidyl serine, phosphatidyl choline, Vitamin D3 and Vitamin K1; and
   (f) adenosine triphosphate (ATP) or a compound which induces generation of cyclic adenosine 3'5'monophosphate cAMP in situ or cyclic quanosina monophosphate (cGMP) in situ.

2. The composition of claim 1 wherein component (f) comprises forskolin.

3. The composition of claim 2 further comprising glycerol monolaurate.

4. The composition of claim 3 further comprising dehydroepiandosterone.

* * * * *